United States Patent [19]

Vinogradov et al.

[11] Patent Number: 4,651,748

[45] Date of Patent: Mar. 24, 1987

[54] METHOD AND DEVICE FOR DETERMINING STATE OF CARDIOVASCULAR SYSTEM

[75] Inventors: Alexei V. Vinogradov; Inna I. Makarova, both of Moscow; Jury N. Alexandrov, Dolgoprudny Moskovskoi; Viktor A. Gaiaktionov, Dolgoprudny Moskovskoi; Jury P. Ozersky, Dolgoprudny Moskovskoi, all of U.S.S.R.

[73] Assignee: Fiziko-Tekhnitchesky Institute, Dolgoprudny, Moskovskoi, U.S.S.R.

[21] Appl. No.: 690,196

[22] PCT Filed: Apr. 13, 1984

[86] PCT No.: PCT/SU84/00020

§ 371 Date: Dec. 14, 1984

§ 102(e) Date: Dec. 14, 1984

[87] PCT Pub. No.: WO84/04032

PCT Pub. Date: Oct. 25, 1984

[30] Foreign Application Priority Data

| Oct. 10, 1980 | [SU] | U.S.S.R. | 3005063 |
| Dec. 31, 1980 | [SU] | U.S.S.R. | 3242870 |
| Dec. 31, 1980 | [SU] | U.S.S.R. | 3261691 |
| Apr. 15, 1983 | [SU] | U.S.S.R. | 3577503 |
| Aug. 3, 1983 | [SU] | U.S.S.R. | 3628069 |
| Jul. 24, 1984 | [IT] | Italy | 48623 A/84 |

[51] Int. Cl.$^4$ ............................................. A61B 5/02
[52] U.S. Cl. ..................................... 128/680; 128/682; 128/686
[58] Field of Search ........ 128/679, 681, 686, 691–694, 128/900

[56] References Cited

U.S. PATENT DOCUMENTS

| 3,871,359 | 3/1975 | Pacela | 128/693 |
| 3,903,872 | 9/1975 | Link | 128/681 |
| 4,140,110 | 2/1979 | Jansen et al. | 128/681 |
| 4,245,650 | 1/1981 | Welker et al. | 128/696 |

FOREIGN PATENT DOCUMENTS

| 1000603 | 2/1952 | France | 128/679 |
| 2352530 | 12/1977 | France | 128/681 |
| 8201121 | 4/1982 | Int'l Pat. Institute | 128/681 |
| 8201122 | 4/1982 | World Int. Prop. O. | 128/681 |

OTHER PUBLICATIONS

Darling, R. C. et al., "Quantitative Segmental Pulse Volume Recorder", Surgery Dec. 1972, vol. 72, No. 6, pp. 873–887.

Excerpts from Biophysical Fundamentals of Blood Circulation and Clinical Methods for . . . , N. N. Savitsky, pp. 141–144, 150, 151, 1974.

Excerpts From Analog-Digital Converters, Gitis et al., pp. 226–228, 1981.

Arterial Oscillograph, USSR Ministry of Health, 1963.

Excerpts From Design of Radioelectronic Equipment Built Around Integrated Circuits, Bakhtiarov et al., pp. 167–168, 1980.

*Primary Examiner*—Kyle L. Howell
*Assistant Examiner*—Francis J. Taworski
*Attorney, Agent, or Firm*—Fleit, Jacobson, Cohn & Price

[57] ABSTRACT

A method for determining the state of the cardiovascular system by measuring a quantitative blood supply parameter for each body part being investigated, which corresponds to a sum total of the absolute areas of all positive and negative half-waves of the first time derivative of pulsed fluctuations of pressure in the blood vessel of the body part being investigated, calculating the sum of these parameters and ratios between them for selected combinations of body parts and comparing these quantitative parameters, as well as their sums and ratios with statistical average ranges established for respective blood supply parameters and their sums and ratios for healthy organisms and organisms with known pathologies, the result of the comparison being indicative of the state of the cardiovascular system of the organism being investigated.

The method is carried out with the aid of a device comprising blood supply measuring channels (5) in a number equal to that of body parts being investigated, each of said channels (5) incorporating an occluding cuff (2)

(Abstract continued on next page.)

for applying pressure generated by a variable pressure source (1) to a body part being investigated. The pressure is applied through an air distributor (7). The device further contains a tachooscillation unit (3) for separating the first time derivative of the pulsed pressure fluctuations in the occluding cuff (2), a blood supply determination unit (6), and a recording unit (4). It also contains a computing unit (29) which calculates sums of quantitiative blood supply parameters and ratios between them, and compares these with statistical average ranges.

18 Claims, 21 Drawing Figures

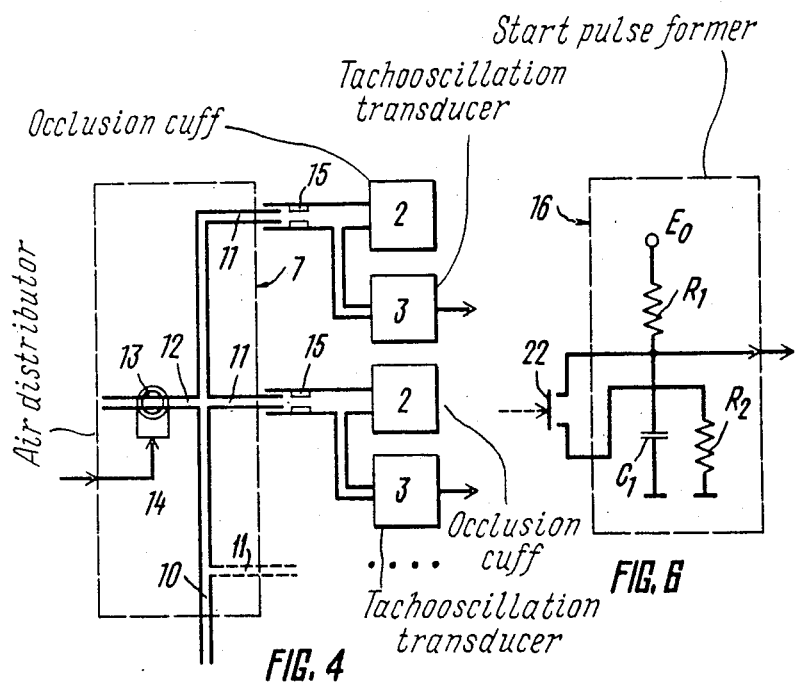
FIG. 4
FIG. 6
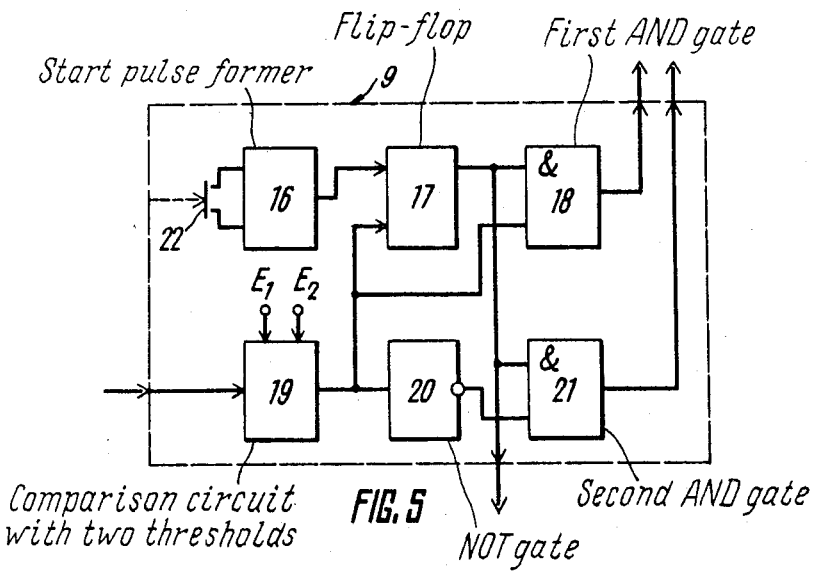
FIG. 5

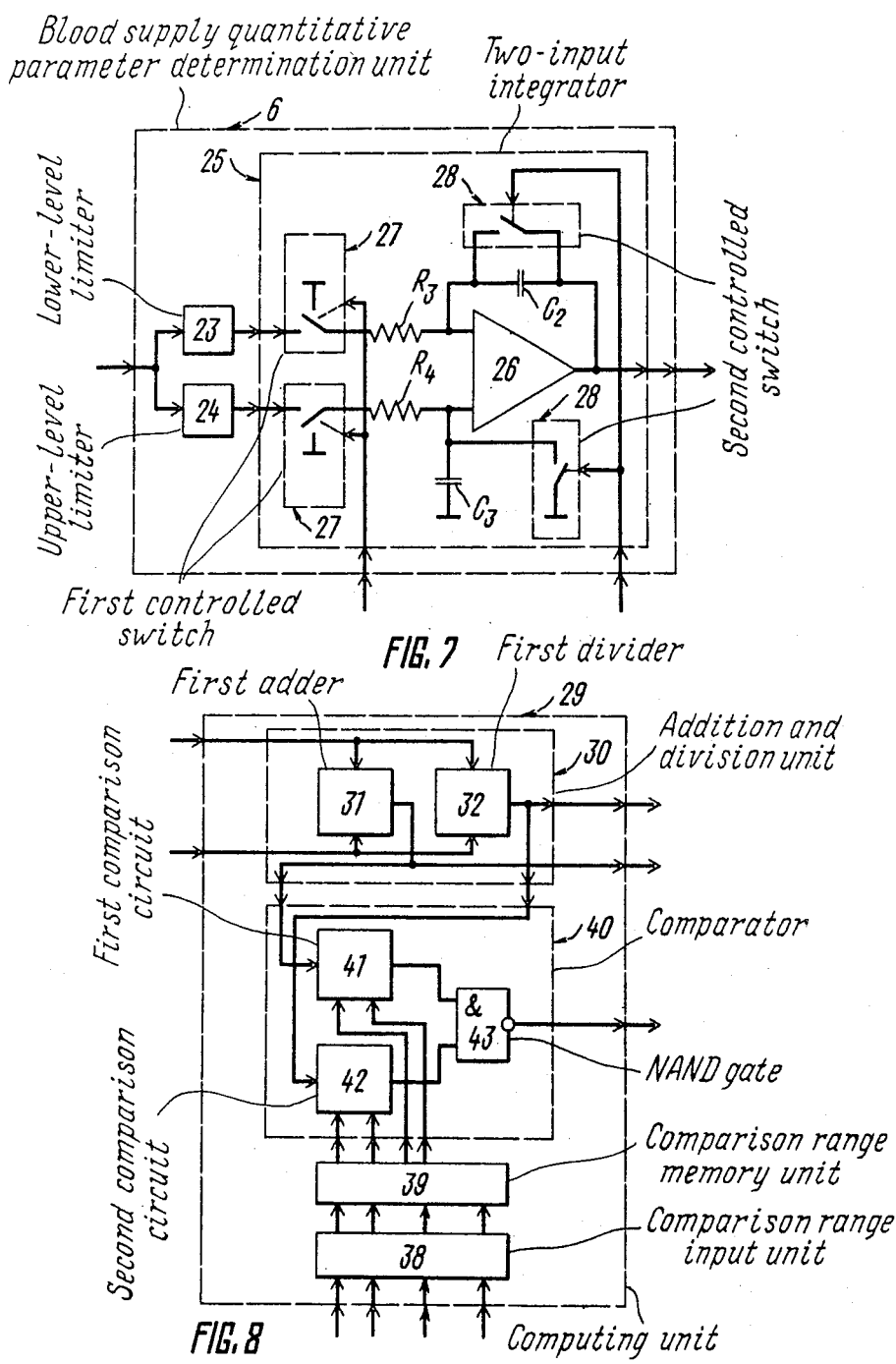

METHOD AND DEVICE FOR DETERMINING STATE OF CARDIOVASCULAR SYSTEM

TECHNICAL FIELD

The present invention relates to medicine and is more particularly concerned with noninvasive methods and devices for determining the state of the cardiovascular system of living organisms by measuring, recording and analyzing the hemodynamic parameters of that system.

PRIOR ART

The state of the cardiovascular system of man and warm-blooded animals depends on a number of factors which include the cardiac action, the state of the blood vessels of different organs, and the nervous regulation of the organism. It is determined through the use of various methods and devices, mostly of the non-invasive type which is the simplest and safest.

There is known a method and device for non-invasive determination of the state of the cardiovascular system of a living organism according to International U.S. Application of Apr. 15, 1982, PCT WO 82/01122, IPC-$^3$A61B 5/02, 5/05.

This method is based on measuring certain hemodynamic parameters of the cardiovascular system and carried out as follows. Four electrodes of an impedance plethysmograph (rheograph) are attached to a part of a subject's body which has to be investigated. Variable pressure is applied to the artery of another part of the subject's body by varying pneumatic pressure in an occlusion cuff enveloping that part. The rheograph measures the electric resistance of the flow of blood through the blood vessel of the part under investigation and its first derivative when the pneumatic pressure in the cuff, which changes due to the pulsation in the vessel, as at its maximum, minimum, and mean levels. These levels are also measured, and so is the conductivity of the blood. On the basis of formulas known from the theory of hemodynamics and the theory of electric circuits, as well as some information on the subject, such as age, sex, weight, and blood conductivity, the results of the measurements are used to calculate various hemodynamic parameters of the cardiovascular system, including the amount of blood ejected by the heart, the cardiac output, the flowrate of blood in the vessel of the part being investigated, the modulus of elasticity of the wall of that vessel, etc. All these values are recorded and serve to determine the state of the subject's cardiovascular system.

The above method is carried out with the aid of a device comprising an electric resistor and its first time derivative measuring channel, an arterial pressure control and measuring channel, a unit for input of data on a patient, as well as a processor and a display which are placed in series. The outputs of said channels and of the data input unit are connected to respective inputs of the processor. The electric resistor and its first time derivative measuring channel is a rheograph with four electrodes. The arterial pressure control and measuring channel comprises a variable pressure source and an occlusion cuff with a pressure sensor which are connected in series.

The method and device in question are disadvantageous in that they fail to provide for a well-differentiated and trustworthy diagnosis of each diseases of the cardiovascular system as ischemia of the heart, atherosclerosis of peripheral arteries, neurocirculatory asthenia; and some others. This is due to a low accuracy of determining the chosen hemodynamic parameters, which, in turn, is accounted for by great errors in measuring the electric resistance of the blood flow with the aid of a rheograph. Such errors result from external effects, namely, the resistance of the contacts between the electrodes and the patient's body and the resistance of other body tissues.

The above method and device are further disadvantageous in that they do not lend themselves to screening.

There are known a method and device for determining the state of the cardiovascular system of living organisms by measuring the arterial blood pressure according to U.S. Pat. No. 4,140,110 of Feb. 20, 1979, IPC A61B 5/02.

This method consists in applying a growing pressure to a part of a subject's body being investigated, which is done by varying pneumatic pressure in an occlusion cuff enveloping that part of the body. The pressure applied to the part under investigation is measured. At a certain instant, the blood pressure is also measured and recorded as the systolic pressure. The instant at which the blood pressure is measured is determined by forming a signal corresponding to the first time derivative of the pulsed pressure fluctuations in the cuff due to the pulsation of blood in the blood vessel of the part being investigated. The signal is referred to as tachooscillation which is used to form a current control signal. The systolic blood pressure is recorded at a time when the value of the control signal is equal to about one half of its maximum magnitude and when the pressure applied to the cuff is greater than the pressure at an instant the control signal is at its maximum. The systolic blood pressure thus measured and recorded is used as the basis for evaluating the state of the cardiovascular system of the patient.

The method is carried out with the aid of a device which comprises in a series arrangement a channel for measuring pressure applied to the part of the body being investigated, a recording unit, and a control channel. The pressure measuring channel comprises in a series arrangement a variable pneumatic pressure source, an occluding cuff, a pressure sensor for measuring pressure in the cuff, and a cuff pressure averaging and interpolation unit. The control channel comprises in a series arrangement a differentiator which serves for the separation of tachooscillations, a control signal forming unit, and a variable pressure source switch-off unit. The input of the differentiator serves as the input of the control channel and is connected to the output of the cuff pressure sensor. The second input of the control signal forming unit is connected to the control input of the averaging and interpolation unit.

The method and device are disadvantageous in their low yield of information and limited functional capabilities. Being intended for measuring arterial blood pressure alone, they fail to provide for a well-differentiated and trustworthy diagnosis of many diseases. Although the device contains a tachooscillation separation unit, tachooscillation only serves to form a signal for determining an instant whereat the arterial pressure is measured by the pressure measuring channel. Thus the device makes only a limited use of the information tachooscillation can provided with regard to the state of the cardiovascular system.

The prototypes of the method and device for determining the state of the cardiovascular system of a living organism in accordance with the present invention are the method and device according to International USSR Application of Apr. 15, 1982, PCT WO 82/01121, IPC A61B 5/02.

This method consists in applying variable pressure to a part of a subject's body being investigated in the area of the blood vessel of that part. Variable pressure is applied by varying pneumatic pressure in an occlusion cuff enveloping the part to be investigated. The pressure applied to the part being investigated is measured. Pressures corresponding to certain instants are recorded as systolic, diastolic and mean blood pressures. The instants whereat these pressures are measured and recorded are determined with the aid of a signal corresponding to the first time derivative of the pulsed pressure fluctuations in the cuff, which are due to pulsations of the blood in the blood vessel of the body part being investigated. The signal is tachooscillation which is used to form a current control signal. The systolic blood pressure is recorded at a time when the value of the control signal is equal to about one half of its maximum magnitude and when the pressure applied to the occlusion cuff is greater than the pressure at an instant the control signal reaches its maximum. The mean blood pressure is the pressure recorded at a time when the control signal reaches its maximum value. The diastolic pressure is the pressure recorded at a time when the value of the control signal is about one half of its maximum magnitude and when the pressure applied to the occlusion cuff is less than the pressure at an instant the control signal reaches it maximum value. The three arterial blood pressure levels are used to determine the state of the cardiovascular system of the patient.

The method is carried out with the aid of a device which comprises in a series arrangement a channel for measuring the pressure applied to the body part being investigated, a recording unit, and a control channel. The pressure measuring channel comprises in a series arrangement a variable pneumatic pressure source, an occlusion cuff, a pressure sensor for measuring the pressure in the occlusion cuff, a memory unit, and a switching unit. The control unit comprises in a series arrangement a tachooscillation unit, a control signal forming unit, and a control unit whose output is connected to the control input of the variable pneumatic pressure source and a respective input of the memory unit. The tachooscillation unit is pneumatically connected to the occluding cuff. The output of the control signal forming unit is connected to the control inputs of the memory unit and switching unit.

The device and method under review are disadvantageous in their low output of information and limited functional capabilities, because even the three arterial blood pressure levels that are measured fail to provide for a well-differentiated and trustworthy diagnosis of various diseases of the cardiovascular system. The method and device fail to assist a physician in selecting the types and doses of drugs for individual patients and analyzing the effects of different factors, such as stress, on living organisms. The method and device make but a limited use of the information contained in tachooscillation which only serves to form a signal for determining instants whereat the three above-mentioned blood pressure levels are recorded. Apart from blood pressure, the method and device yield no hemodynamic data.

DISCLOSURE OF THE INVENTION

It is an object of the present invention to provide a non-invasive method and device for determining the state of the cardiovascular system, which would furnish a well-differentiated and trustworthy diagnosis of the state of the cardiovascular system and have a wide range of functional capabilities due to the use of the extensive information content of tachooscillation.

The invention provides a method for determining the state of the cardiovascular system, which comprises the steps of applying variable pressure to at least one part of a living organism being investigated in the area of the blood vessel of that part, and, as the pressure changes, separating a signal corresponding to the first time derivative of the pulsed fluctuations due to the pulsations of pressure in the blood vessel of the body part being investigated, the signal being tachooscillation, which method is characterized, in accordance with the invention, in that the quantity corresponding to the sum total of the absolute values of the areas of all positive and negative tachooscillation half-waves is measured and recorded as a quantitative parameter evaluating the supply of blood to the body part being investigated, and in that the same quantitative parameter is determined in the same way for the same body part of healthy organisms and organisms with known pathologies, whereupon the statistical data thus obtained is used to determine the corresponding statistical average ranges of change of said quantitative parameter for these organisms, which is followed by quantitatively evaluating in the above manner the supply of blood to the body part being investigated and comparing it with said statistical average ranges, the corresponding range being indicative of a deviation from the norm with regard to the supply of blood to the body part under investigation, which deviation points to a pathologic change in the cardiovascular system of the organism being investigated.

The method according to the invention is totally harmless to living organisms and yet makes it possible to measure and record a new hemodynamic parameter, namely, the level of the supply of blood to the body part being investigated, which parameter contains information on the cardiac action and the state of the cardiovascular system with due regard to the effectiveness of the nervous regulation of the cardiovascular system.

It is essential that any changes in the state of the cardiovascular system related to a specific type and phase of a disease and the effects on the organism of drugs and physical and emotional factors, such as stress, lead to corresponding changes of the above-mentioned hemodynamic parameter which is thus a more sensitive characteristic and a more comprehensive indication of the state of the cardiovascular system than such parameters as the arterial pressure, temperature, and electric resistance of the flow of blood through the blood vessel of the body part being investigated.

In investigating at least two parts of a body, it is preferred that the quantitative parameter of the supply of blood of these parts be determined simultaneously, and that the sum total of, and the ratios between, the measured quantities corresponding to the sums total of the absolute values of the areas of all positive and negative half-waves of separated tachooscillations be calculated for each part of the body being investigated, which sum total and ratios are recorded as quantitative parameters of the total supply of blood to all the body parts being investigated and the asymmetry between the supply of blood to these parts; it is further preferred that the total supply of blood to the same parts of the body and the asymmetry between the supply of blood to these parts be determined for healthy organisms and organisms with known pathologies, and that the statistical data thus obtained be used to determine the statistical average ranges of change of said quantitative parameters for these organisms, whereupon the quantitative parameters of the total supply of blood to the same parts of the body and the asymmetry between the supply of blood to these parts are determined in the same way for the organism being investigated and compared with the above-mentioned ranges in order to use the set of the corresponding ranges as an indication of deviation from the norm with regard to the supply of blood to the body parts being investigated and of pathologic changes in the state of the cardiovascular system of the organism being investigated.

It is also possible to calculate the ratio between each quantity measured for the body part being investigated and the sum total of all quantities measured for all the body parts being investigated, and record these ratios as quantitative parameter of the relative supply of blood to the body parts being investigated; it is preferred that similar quantitative parameters be obtained for healthy organisms and organisms with known pathologies, whereupon the statistical data thus obtained are used to establish corresponding statistical average ranges of change of said quantitative parameters for these organisms, after which the desired quantitative parameters are established for the organism being investigated and compared with said ranges in order to use the set of corresponding ranges as an indication of deviations from the norm with regard to the supply of blood to the body parts being investigated and pathologic changes in the state of the cardiovascular system of the organism being investigated.

This makes it possible to measure, record and analyze new hemodynamic parameters, namely, the quantitative parameters of the supply of blood to each body part being investigated, the total supply of blood to all the body parts being investigated, the asymmetry between the supply of blood to different body parts, and the relative supply of blood to the body parts being investigated.

The result is a more correct conclusion with regard to the presence or absence of pathology in the cardiovascular system. The invention makes it possible to narrow down the list of all possible diseases to one specific disease. This means a well-differentiated diagnosis which becomes more and more trustworthy with an increase of body parts to undergo investigation, provided these parts are selected rationally.

In investigating several pairs of symmetrical body parts, it is preferred that one calculate the sum total of measured quantities for each pair of the symmetrical body parts being investigated, the sum total of quantities measured for all the left body parts being investigated, the sum total of quantities measured for all the right body parts being investigated, the ratio between these sums, and the ratio between each of the sums thus calculated and the sum total of the quantities measured for all the body parts being investigated, whereupon all the sums and ratios thus calculated are recorded as quantitative parameters of the total and relative supply of blood to the sets of symmetrical body parts being investigated; it is further preferred that said quantitative parameters be established for healthy organisms and organisms with known pathologies, and that the statistical data thus obtained be used to determine corresponding statistical average ranges of change of said quantitative parameters for these organisms, whereupon said quantitative parameters are determined for the organism being investigated and compared with said ranges in order to use the set of corresponding ranges as an indication of deviations from the norm with regard to the supply of blood to the body parts being investigated and pathologic changes in the state of the cardiovascular system of the organism being investigated.

It is preferred that one also calculate the ratios between each of the sums of quantities measured for a respective pair of symmetrical body parts and the sum total of quantities for one of such pairs, and record all the ratios thus calculated as quantitative parameters of the relative supply of blood to the pairs of symmetrical body parts being investigated against the supply of blood to one of such pairs; it is further preferred that said quantitative parameters be established in a similar manner for healthy organisms and organisms with known pathologies, and that the statistical data thus obtained be used to establish corresponding statistical average ranges of change of said quantitative parameters for these organisms, whereupon the desired quantitative parameters are determined for the organism being investigated and compared with said ranges in order to use the set of corresponding ranges as an indication of deviations from the norm with regard to the supply of blood to the body parts being investigated and the presence of pathologic changes in the cardiovascular system of the organism being investigated.

This makes it possible to use new effective criteria for evaluating the current state of the cardiovascular system, based on the data on the supply of blood to certain sets of symmetrical body parts being investigated in the vertical plane (i.e., the head, and upper and lower extremities) and the horizontal plane (i.e., the left and right extremities, and left and right halves of the body).

The blood supply characteristics differ in healthy and pathologic organisms. Knowing these differences, one can rapidly and correctly determine the disease of the organism being investigated. The above method lends itself to automatic diagnostics and screening. A rational selection of a set of symmetrical and single body parts to be investigated and of a set of quantitative parameters to be used for the determination of the state of the cardiovascular system makes it possible to obtain a desired amount of information on the cardiovascular system of the organism being investigated, and provides for an effective and well-differentiated diagnosis.

In investigating changes with time in the state of the cardiovascular system of a living organism, it is preferred that one compare recorded quantitative parameters with those recorded during preceding investigations, and with statistical average ranges of change of the quantitative parameters for healthy organisms and organisms with known pathologies; it is further preferred that the nature of changes of said parameters between investigations with respect to one another and with respect to said ranges be used as the basis for evaluating the dynamics of the state of the cardiovascular system.

The above procedure makes it possible
  to evaluate the effectiveness of treatment and optimize the selection of the types and doses of drugs and treatment procedures;

to develop new medicinal preparations and drugs and quickly test them on experimental animals without killing the latter;

to forecast the state of an organism under investigation;

to determine vocational aptitudes and monitor the loads on athletes during training and competitions;

to conduct preventive examinations of certain groups of patients, etc.

The above is indicative of extensive functional capabilities of the method according to the invention for determining the state of the cardiovascular system of living organisms.

The method of this invention further makes it possible to measure the time during which tachooscillation in body parts being investigated is separated; in doing so, it is preferred that one calculates the ratio between the sum total of absolute values of the areas of all positive and negative half-waves of tachooscillations separated for each body part being investigated and the duration of the above-mentioned period of time, and record these ratios as quantitative parameters of the supply of blood to the body parts being investigated.

This reduces the error of the quantitative evaluation of blood supply which are due to unstable parameters of the measuring equipment (i.e., of the device for carrying out the method in accordance with the invention). The result is a well-differentiated and trustworthy diagnosis.

In looking for stenosis of arteries in cases of thrombooblierating disorders of lower extremities, it is preferred that the supply of blood to the lower extremity being investigated be measured and recorded successively as variable pressure is applied to different areas of that extremity. Manifest stenosis is diagnosed when a blood supply measurement differs from preceding measurements two- to five-fold; occlusion is registered when the difference is more than five-fold.

The above procedure enables a physician to accurately establish the presence, degree and location of stenosis or occlusion of arteries in cases of thromboobliterating diseases of both upper and lower extremities.

In the case of a preventive checkup of the state of the cardiovascular system, it is preferred that variable pressure be simultaneously applied to the left and right arms of the patient in symmetrical areas, namely, to the brachial arteries of the shoulders, and that the quantitative parameters of the total supply of blood to both arms and the asymmetry in the supply of blood to the left and right arms be measured and recorded, whereupon the data thus obtained is compared with the statistical average ranges of change of the same parameters for the same parts of the body of healthy subjects of the same sex and age group. A discrepancy between all the patient's parameters, or at least one of them, and the corresponding ranges is indicative of a pathologic change in the cardiovascular system of the patient and points to the necessity of a detailed medical examination.

Thus the invention provides for a rapid and accurate diagnosis of pathologic changes of the cardiovascular system of patients, which, in turn, makes it possible to conduct large-scale preventive examinations of certain groups of subjects, such as pilots, drivers, etc. The invention also enables patients themselves to check up the state of their cardiovascular system.

In diagnosing atherosclerosis of the arteries which supply blood to the lower extremities, it is preferred that variable pressure be applied simultaneously to symmetric areas on the left and right sides of the patient's head in the zone of the left and right temporal areas; variable pressure is also applied symmetrically to the brachial arteries of the shoulders and to the arteries of both shins. The quantitative parameter of the total supply of blood to all the six parts of the body is measured and recorded, and so is the quantitative parameter of the relative supply of blood to both legs which is compared with the total supply of blood to both sides of the head. The data thus obtained is compared with the statistical average ranges of change of respective parameters for patients of the same sex and age group suffering from atherosclerosis of the arteries supplying blood to the lower extremities, which ranges amount to 40 to 80 percent of the statistical average value of the quantitative parameter of the total supply of blood to all the six parts of the body in healthy subjects and are between 0.3 and 2.0 with regard to quantitative parameter of the relative supply of blood to both legs of the patient. If the patient's parameters are within the corresponding ranges he or she clearly suffers from atherosclerosis of arteries supplying blood to the lower extremities.

This provides for a rapid and accurate diagnosis of atherosclerosis of arteries supplying blood to lower extremities. Moreover, the diagnosing can be automated.

The invention further provides a device for determining the state of the cardiovascular system, which comprises a variable pressure source pneumatically connected to an occlusion cuff and a tachooscillation transducer, as well as a recording unit, the device being characterized, according to the invention, in that it contains at least one blood supply quantitative parameter measuring channel comprising said variable pressure source, occlusion cuff and tachooscillation unit, as well as a blood supply quantitative parameter determination unit whose signal input is connected to the output of the tachooscillation transducer, whereas the output of the blood supply quantitative parameter determination unit, which serves as the output of the blood supply quantitative parameter measuring channel, is connected to a respective input of the recording unit.

In investigating at least two body parts, it is preferred that the number of blood supply quantitative parameter measuring channels be equal to that of body parts being investigated, in which case the variable pressure source is common for all the blood supply quantitative parameter measuring channels and the device includes an air distributor, as well as a pressure transducer and a control unit placed in series, the occlusion cuff of each blood quantitative parameter supply measuring channel being pneumatically connected to a respective outlet of the air distributor whose inlet is connected to the outlet of the variable pressure source and the input of the pressure transducer, the first output of the control unit being connected to respective control inputs of the variable pressure source, air distributor and recording unit, the second and third outputs of the control unit being connected to the first and second inputs, respectively, of the blood supply quantitative parameter determination units of all said channels.

It is preferred that the device include a computing unit comprising an addition and division unit whose inputs serve as the inputs of the computing unit and are connected to outputs of the respective blood supply quantitative parameter measuring channels, whereas the outputs of the addition and division unit serve as the outputs of the computing unit and are connected to respective inputs of the recording unit.

In investigating two body parts, it is preferred that the addition and division unit comprise a first adder and a first divider of quantitative blood supply parameters, their respective like inputs being interconnected and serving as the inputs of the addition and division unit, whereas their outputs serve as the outputs of the addition and division unit.

In investigating three pairs of symmetrical body parts, it is preferred that the addition and division unit contain a first adder and a first divider for each pair of blood supply quantitative parameter measuring channels intended for measuring the supply of blood to a respective pair of body parts, their like inputs being interconnected and serving as the inputs of the addition and division unit, a second adder for said channels corresponding to all the left body parts being investigated, its inputs being connected to respective inputs of the addition and division unit, a third adder for said channels corresponding to all the right body parts being investigated, its input being connected to respective inputs of the addition and division unit, a fourth adder and a second divider of quantitative blood supply parameters of all the left body parts and of the total supply of blood to all the right body parts being investigated, their like inputs being interconnected and respectively connected to the outputs of the second and third adders, the outputs of all the adders and dividers serving as respective outputs of the addition and division unit.

It is preferred that the addition and division unit further include two third dividers for the three pair of blood quantitative parameter supply measuring channels corresponding to the three pair of body parts being investigated, the first inputs of the third dividers being connected to the output of the first adder for one pair of said channels corresponding to one pair of symmetrical body parts being investigated, the second inputs of the third dividers being respectively connected to the outputs of the first adders for the other two channels, the outputs of the third adders serving as respective outputs of the addition and division unit.

It is preferred that the computing unit additionally include in a series arrangement a comparison range input unit, a comparison range memory unit, and a comparator whose other inputs are connected to respective outputs of the addition and division unit, the inputs of the comparison range input unit serving as respective inputs of the computing unit, the outputs of the comparator serving as respective outputs of the computing unit.

In investigating two body parts, it is preferred that the comparator comprise comparison circuits for comparison with the first and second comparison ranges, respectively, and a NAND gate whose inputs are respectively connected to the outputs of said comparison circuits, the signal input of the comparison circuit for comparison with the first comparison range serving as a respective input of the comparator and being connected to the output of the first blood supply parameters adder of the addition and division unit, the signal input of the comparison circuit for comparison with the second comparison range serving as a respective input of the comparator and being connected to the output of the first blood supply parameters divider of the addition and division unit, the first and second threshold inputs of the comparison circuits for comparison with the first and second comparison ranges serving as respective inputs of the comparator and being connected to respective inputs of the comparison range memory unit, the output of the NAND gate serving as the output of the comparator and a respective output of the computing unit.

It is preferred that the device include a tachooscillation separation time measuring unit, and that each blood supply measuring channel contain a divider for dividing a measured quantitative blood supply parameter by a measured duration of the separation of tachooscillations, its first input being connected to the output of the blood supply quantitative parameter determination unit, the second input of said divider being connected to the output of the tachooscillation separation time measuring unit, while its output serves as the output of the blood supply quantitative measuring measuring channel, the input of the tachooscillation separation time measuring unit being connected to a third output of the control unit.

It is further preferred that each occlusion cuff comprise a sheath with an elastic pocket and a means for fastening the cuff on a patient's body, as well as a pneumatic compression band placed in the pocket of the cuff's sheath and a sensitive elastic compression band placed in the pocket of the cuff's sheath between the pneumatic compression band and the pocket wall next to the patient's body, the sensitive compression band being separated from the pneumatic compression band by a flexible partition and connected to the input of the tachooscillation transducer, the pneumatic compression band being directly connected to a respective outlet of the air distributor.

BRIEF DESCRIPTION OF DRAWINGS

FIG. 4 is a simplified pneumoelectric diagram of an exemplary embodiment of the air distributor in accordance with the invention;

FIG. 5 is a functional diagram of an exemplary embodiment of the control unit in accordance with the invention;

FIG. 6 is an electric diagram of an exemplary embodiment of the start pulse former with a start button in accordance with the invention;

FIG. 7 is a simplified electric circuit of an exemplary embodiment of the blood supply quantitative parameter determination unit in accordance with the invention;

FIG. 8 is a functional diagram of the computing unit of a device according to the invention intended to investigate two parts of a body;

BEST MODE FOR CARRYING OUT THE INVENTION

The method according to the invention for determining the state of the cardiovascular system is as follows.

Figure 1:
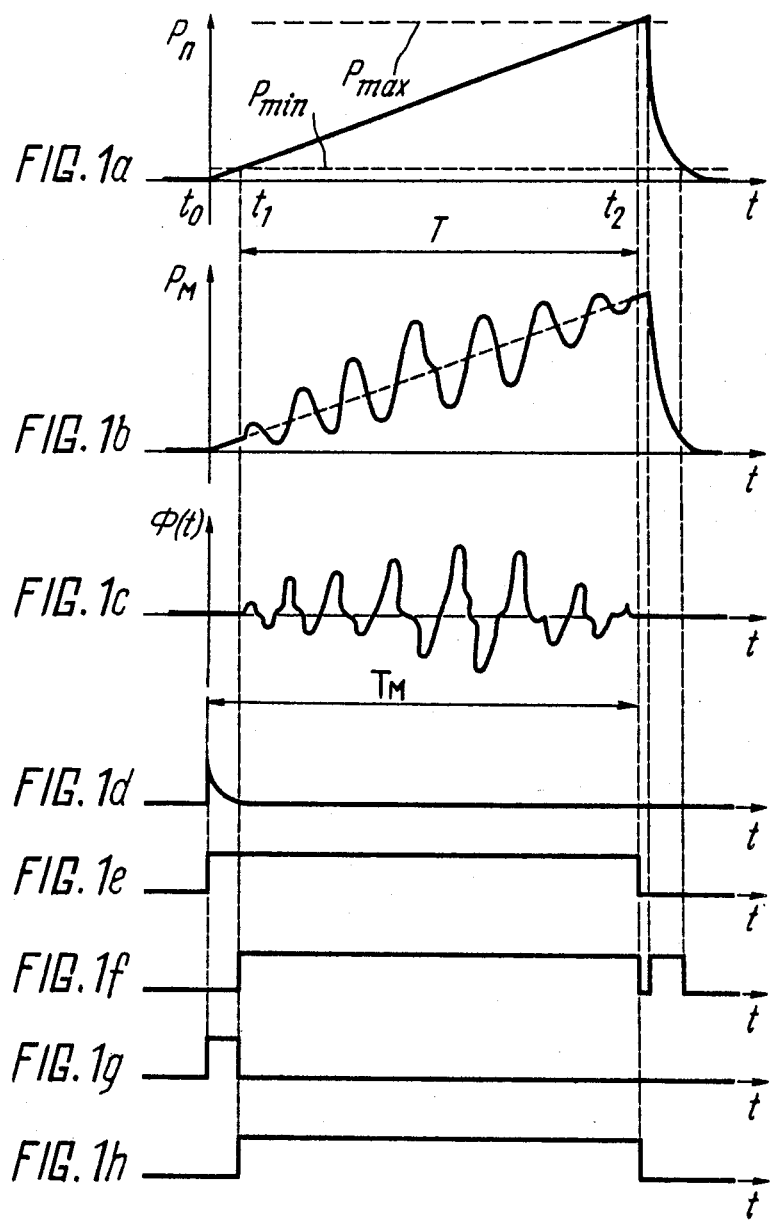
FIG. 1 is a set of time plots illustrating the method and device in accordance with the invention for determining the state of the cardiovascular system.

In investigating one body part of a living organism, such as a human being or a warm-blooded animal, the investigation procedure begins with fastening an occlusion cuff on this body part. The cuff is normally attached to the right or left shoulder in the brachial artery area. The cuff is then connected to a variable pressure source, such as an air compressor. Arranged at the outlet of the compressor is a converter means for converting the constant pneumatic pressure to pressure varied according to a prescribed pattern. The pressure applied to the cuff is linearly raised at a rate of 3 to 7 mm of mercury per second, as is shown in FIG. 1a where time t is plotted on the x-axis and pressure P⊓ applied to the cuff, which is measured in arbitrary units and is excessive in comparison with the atmospheric pressure, is laid off along the y-axis. The instant $t_o$ is the start of a change of pressure P⊓. When P⊓ exceeds the pressure $P_{min} \leq 50$ mm of mercury, the cuff compresses the body part being investigated and the pressure P⊓ is applied to that part in the area of its blood vessel. From this instant, which is designated as $t_1$ in FIG. 1a, and till an instant when the pressure P⊓ completely constricts the blood vessel of the body part enveloped by the cuff, the full variable pressure $P_m$ in the occluding cuff is the sum of the pressure P⊓ applied to the body part being investigated and the pulsed pressure fluctuations caused by the pulsation of blood in the vessel which is transmitted through the wall of that vessel and the tissue to the occlusion cuff. FIG. 1b shows the change of the pressure $P_m$ with time. In FIG. 1b, time t is laid off along the x-axis and the complete variable pressure $P_m$ in the occluding cuff, measured in arbitrary units, is plotted as the ordinates.

A differential pressure sensor pneumatically connected to the occlusion cuff is used to separate a signal corresponding to the first time derivative of the pulsed pressure fluctuations in the cuff, which are due to the pulsation of blood in the blood vessel of the body part being investigated. This signal is tachooscillation. The type of tachooscillation as a function of time is presented in FIG. 1c where time t is plotted on the x-axis and the current magnitude $\phi(t)$, measured in arbitrary units, of the separated signal is laid off along the y-axis. The value S, corresponding to the sum total of the absolute areas of all positive and negative half-waves of the separated tachooscillations is measured manually or automatically (electronically). Pressure P⊓ applied to the body part being investigated is raised to a certain maximum level $P_{max} = 200$ to 250 mm of mercury at which the blood vessels of the body part being investigated are fully constricted. As a result, the tachooscillations either disappear or their amplitude becomes negligibly small. The pressure P⊓ is then rapidly reduced to zero in order to restore circulation in the body part being investigated (see FIG. 1a). S meets this condition:

$$S = \int_{t_1}^{t_2} |\phi(t)| dt, \quad (1)$$

i.e., it is equal to the integral of the modulus (the absolute value) of the function $\phi(t)$ over a period of time $T = t_2 - t_1$, where $t_2$ is an instant when P⊓ reaches the maximum level, becoming equal to $P_{max}$ (see FIG. 1a).

S is measured and recorded as a quantitative parameter of the supply of blood to the body part being investigated.

In order to use this quantitative parameter for the determination of the state of the cardiovascular system of a specific organism, one must either have or obtain statistical data on the levels of this quantitative parameter in healthy organisms of the same species, such as man, ape, dog, etc., with due regard for the age group. One must also have similar statistical data on the same organisms with known pathologies, i.e., organisms either suffering from known diseases or exposed to known physical or psychological factors. The above-mentioned quantitative parameter is determined for a large number of healthy organisms of the same species and for organisms with known pathologies. By using mathematical statistics, the statistical data thus obtained is used to establish corresponding statistical average ranges of change of said quantitative parameter for all these organisms. In keeping with the rules of mathematical statistics, the number of healthy organisms and organisms with known pathologies must be great enough to ensure a desired accuracy of the statistical average ranges. The same procedure is then used to determine the quantitative parameter of the supply of blood to the same body part of the organism being investigated, which is compared with the statistical average ranges. A correspondence of the quantitative parameter to one of these ranges is indicative of deviations from the norm with regard to the supply of blood to the body part being investigated and points to a pathologic state of the cardiovascular system of the organism being investigated.

It must be pointed out that a quantitative parameter of the supply of blood to a body part being investigated can be obtained by reducing the pressure P⊓ applied to the occlusion cuff from $P_{max}$ to zero instead of raising it from zero to $P_{max}$ as described above. For this purpose, the pressure in the cuff is raised to the $P_{max}$ level and then linearly reduced to zero. In the latter case, the tachooscillation is of the type shown in FIG. 1c, but it is inverted in time. It must further be pointed out that the pressure P⊓ applied to the occlusion cuff can be varied in other ways. The quantitative blood supply parameters obtained by using the above procedures may vary in their absolute values, wherefore they must be compared with statistical average ranges established while investigating healthy organisms and organisms with known mathologies, provided the pressure P⊓ applied to the occluding cuff is varied according to the same pattern.

In investigating at least two body parts of a living organism, an occlusion cuff is attached to each of these parts. Cuffs can be symmetrically attached, for example, to the right and left shoulders of a patient in the brachial artery areas. The cuffs are then connected to a source (or sources) of variable pressure P⊓ which is simultaneously varied in both cuffs as in the case of investigating one body part. Respective differentiating pressure transducers are used to separate signals corresponding to the first time derivatives of the pulsed pressure fluctuations in the cuffs which are caused by pulsations of blood in the blood vessels of the body parts being investigated. The separated signals are tachooscillations.

For each body part being investigated, one measures the quantity corresponding to the sum total of the absolute values of all areas of positive and negative half-waves of the separated tachooscillations. The quantities thus obtained are recorded as quantitative parameters of the supply of blood to both body parts being investigated. One also calculates the sum total of said quantitative parameters for each body part being investigated, as well as the ratios between these parameters. The sums and ratios are recorded as quantitative parameters $S_\Sigma$ of the total supply of blood to all the body parts being investigated and the asymmetry $A_i$ (where $i = 1, 2, \ldots, n$, n being the number of ratios) of their blood supplies in relation to each other.

In order to use said quantitative parameters for determining the state of the cardiovascular system, statistical data is obtained on the distribution of these quantitative parameters in healthy organisms, and statistical average ranges of change of these quantitative parameters are established.

One then proceeds to determine in the manner described above the same quantitative parameters for the same body parts of the organism being investigated, which are compared with the statistical average ranges. The correspondence is indicative of a deviation from the norm with regard to the supply of blood to each body part being investigated, the total supply of blood to all body parts being investigated, and the difference in the supply of blood to right and left body parts. It is also indicative of a pathologic state of the cardiovascular system of the organism being investigated.

According to an alternative embodiment of the method of this invention, an investigation of two and more body parts includes the calculation of the ratio of each quantity corresponding to the sum total of the absolute values of areas of all positive and negative half-waves of separated tachooscillations for a body part being investigated to a sum total of similar quantities measured for all the body parts being investigated. All the ratios thus calculated are recorded as quantitative parameters $R_j$ ($j = 1, 2, \ldots, m$, where m is the number of quantitative parameters) of the relative supply of blood to the body parts being investigated. This is done in addition to determining the quantitative parameters of the supply of blood to each body part being investigated, the total supply of blood to all the body parts being investigated, and the asymmetry of their blood supply.

The quantitative parameters are compared with statistical average ranges of change of said quantitative parameters for healthy organisms and organisms with known pathologies. The result of the comparison is indicative of the state of the cardiovascular system of the organism being investigated.

The number and type of body parts to be investigated, and the number and type of quantitative parameters may vary in different cases.

In investigating several pair of symmetrical body parts of a living organism, such as man or a warm-blooded animal, an occlusion cuff is attached to each body part being investigated. Cuffs can be symmetrically attached to the right and left sides of the head in the temporal artery areas, the right and left shoulders in the brachial artery areas, and the right and left shins in the area of arteries in the middle of each shin. All the cuffs are connected to a variable pressure source (or sources), whereupon the pressure in each cuff is simultaneously and synchronously varied in the manner described above for the case when one or more body parts are investigated. One measures and records in a similar way quantitative parameters of the supply of blood to each body part being investigated, the total supply of blood to these parts, the relative supply of blood to all these parts, and the asymmetry of the supply of blood to these parts in relation to each other. One also calculates the sum of the measured quantities for each pair of body parts being investigated; in the case being considered, such quantities are calculated for both sides of the head, both arms, and both legs. One further calculates the sum total of the quantities measured for all the left parts of the body being investigated, i.e., the left side of the head, left arm, and left leg. One then calculates the sum total of quantities measured for all the right parts being investigated, i.e., the right side of the head, right arm, and right leg. The ratio between the two latter sums is calculated, and so is the ratio of each sum to the sum total of quantities measured for all the body parts being investigated. All the sums and ratios are recorded as quantitative parameters of the total and relative supply of blood to the symmetrical body parts being investigated.

The quantitative blood supply parameters are then compared with statistical average ranges of change of these values for healthy organisms and organisms with known pathologies. The results of the comparison are indicative of the state of the cardiovascular system of the organism being investigated.

In investigating several pairs of symmetrical body parts, one can use an alternative embodiment of the method according to the invention. The alternative embodiment is characterized in that one additionally calculates the ratio of each sum of quantities measured for a pair of symmetrical body parts being investigated to the sum of quantities measured for one of such pairs. Such ratios are recorded as quantitative parameters of the relative supply of blood to the symmetrical pairs of body parts being investigated in relation to the supply of blood to one of such pairs. For example, in investigating symmetrical parts of human body, such as the right and left sides of the head, the right and left arms, and the right and left legs, one may record the quantitative parameters of the relative blood supply of both arms and both legs in relation to the blood supply of both sides of the head (the distribution of the blood supply in the vertical plane).

The quantitative parameters thus established are compared with statistical average ranges of change of these parameters for healthy organisms and organisms with known pathologies. The results of the comparison are indicative of the state of the cardiovascular system of the organism being investigated.

In investigating the six above-mentioned parts of the body, i.e., the left and right sides of the head, left and right arms, and left and right legs, one can determine and record the following new hemodynamic parameters of the cardiovascular system of the subject:

quantitative blood supply parameters $S_i$ of each body part being investigated, where i is the arbitrary serial number of each body part; for example, the body parts being investigated may be designated as follows: 1—left side of the head, 2—right side of the head, 3—left arm, 4—right arm, 5—left leg, 6—right leg; the values of $S_i$ are calculated by using the formula (1);

the quantitative parameter of the total supply of blood to all the six body parts being investigated $$S_\Sigma = S_1 + S_2 + S_3 + S_4 + S_5 + S_6; \quad (2)$$

the quantitative parameter of the total blood supply of each pair of symmetrical body parts, i.e., for the head $$S_{12} = S_1 + S_2, \quad (3)$$

for the arms $$S_{34} = S_3 + S_4, \quad (4)$$

and for the legs $$S_{56} = S_5 + S_6; \quad (5)$$

the quantitative parameter of the total supply of blood to all the left body parts being investigated $$S_{135} = S_1 + S_3 + S_5; \quad (6)$$

the quantitative parameter of the total supply of blood to all the right body parts being investigated $$S_{241} = S_2 + S_4 + S_6; \quad (7)$$

the quantitative parameter of the asymmetry of blood supply for each pair of body parts being investigated, i.e., for the left and right sides of the head $$A_{12} = S_1/S_2, \quad (8)$$

for the left and right arms $$A_{34} = S_3/S_4 \quad (9)$$

and for the left and right legs $$A_{56} = S_5/S_6; \quad (10)$$

the quantitative parameter of the relative supply of blood to all the left body parts versus the total supply of blood to all the right body parts $$A_\Sigma = S_{135}/S_{246}; \quad (11)$$

the quantitative parameter of the relative blood supply of each body part being investigated, expressed in terms of percentage, i.e.

$$R_1 = S_1/S_\Sigma, \ R_3 = S_3/S_\Sigma, \ R_5 = S_5/S_\Sigma, \ R_2 = S_2/S_\Sigma, \\ R_4 = S_4/S_\Sigma, \ R_6 = S_6/S_\Sigma; \quad (12)$$

the quantitative parameter of the supply of blood of each pair of symmetrical body parts being investigated, i.e., the head, arms, and legs $$R_{12} = S_{12}/S_\Sigma, \ R_{34} = S_{34}/S_\Sigma, \ R_{56} = S_{56}/S_\Sigma; \quad (13)$$

the quantitative parameter of the relative blood supply of all the left and right parts of the body $$R_{135} = S_{135}/S_\Sigma, \ R_{246} = S_{246}/S_\Sigma; \quad (14)$$

the quantitative parameter of the relative blood supply of the symmetrical body parts being investigated, which parameter is compared, for example, with the total supply of blood to the head:

$$B_{12} = S_{12}/S_{12} = 1, \ B_{34} = S_{34}/S_{12}, \ B_{56} = S_{56}/S_{12} \quad (15)$$

The type and number of body parts to be investigated, as well as the type, number and combinations of quantitative parameters used in the investigation are determined by specific circumstances.

According to the latest research, a differential diagnosis of a large number of diseases of the cardiovascular system of man is best performed by investigating the above-mentioned six parts of the body and by analyzing quantitative parameters derived from (2) . . . (15).

One may also use other combinations of body parts to be investigated. It is possible, for example, to investigate several pairs of symmetrical body parts and some single parts. In the case of a differential diagnosis of sexual impotence with a view to establishing a vascular genesis of the diseases, variable pressure can be simultaneously applied through the use of occlusion cuffs attached to the head, arms, and penis of the patient. The relative blood supply parameters of these parts of the body may reveal that erection is impossible due to a pathology of the cardiovascular system, which makes it possible to select a suitable treatment procedure.

In the case of warm-blooded animals, one may investigate the head, the fore and hind legs, and the tail. The quantitative parameters of relative blood supply may be the ratios of the blood supply parameters for individual body parts or combinations thereof to both the sum total of quantities measured for all body parts being investigated and the sum total of quantities measured for one pair of symmetrical body parts being investigated, such as the head or hind extremities, or to a quantity measured for a single body part, such as the tail, etc.

In investigating the changes with time in the state of the cardiovascular system of a patient undergoing a prolonged course of treatment, or of an athlete, quantitative blood supply parameters should be measured and recorded periodically. The quantitative blood supply parameters are determined in accordance with one of the above embodiments of the method of this invention for the determination of the state of the cardiovascular system. The quantitative parameters measured and recorded during preceding and subsequent investigations are compared with one another and with statistical average ranges of change of these blood supply parameters for healthy organisms and organisms with known pathologies. The nature and rate of the change of the quantitative blood supply parameters are indivative of the nature of changes of the state of the cardiovascular system of the subject. For example, if the quantitative blood supply parameters shift during treatment from the statistical average ranges established for organisms suffering from a given disease toward the ranges established for healthy organisms, the inference is that the choice of treatment is correct. The rate of change of the quantitative blood supply parameters is indicative of the effectiveness of treatment. Thus it is possible to forecast changes in the state of a patient. It is possible, for example, to forecast the probability of a shock and the time of its arrival, and take the necessary measures.

The selection of time intervals between investigations, and of the type and number of quantitative blood supply parameters are determined by the type of disease and the nature of investigation.

According to another preferred embodiment of the method according to the invention, one measures the time during which tachooscillations are separated in the body parts being investigated. This is done apart from applying variable pressure to body parts being investigated in the blood vessel areas, separating tachooscillations, and measuring quantities corresponding to sums total of the absolute values of the areas of all positive and negative tachooscillation half-waves for each body part being investigated. One then measures the ratios between each measured quantity and the duration of said time interval, which ratios are recorded as quantitative blood supply parameters of the body parts being investigated and used in accordance with one of the procedures described above. Thus the embodiment in question is characterized in that all measured quantities are related to the time of measurement. Such an approach leads to a greater accuracy of determining quantitative blood supply parameters. The factors behind the improvement are as follows. The tachooscillation time for each body part being investigated is determined by the time T during which pressure in the occlusion cuffs rises from $P_{min}$ to $P_{max}$ (see FIG. 1a). In practice, the values of T may vary by as much as 15 to 30 percent from measurement to measurement, which is due to unstable parameters of the variable pneumatic pressure source and unstable parameters of the system for supplying air to the occluding cuffs, caused by clogging of air throttles of the line through which air is fed to the cuffs, and other reasons. Variations of T account for changes in the number of half-waves in the separated tachooscillations, which lead to a change of the sum total of the absolute areas of their positive and negative half-waves. Relating these sums to T makes it possible to reduce the differences in quantitative blood supply parameters due to the above-mentioned factors.

In looking for stenosis of arteries in cases of thromboobliterating diseases of lower extremities, quantitative blood supply parameters of the lower extremity being investigated should be measured and recorded several times by applying variable pressure to different areas of the extremity being investigated. Measurements are preferably started in the upper half of the extremity and continued by shifting to the shin. For this purpose the occlusion cuff is appropriately shifted over the extremity. Recorded quantitative blood supply parameters are compared with previously recorded values thereof. The comparison points to manifest stenosis if the difference between recorded parameters and preceding measurements is 2- to 5-fold. Occlusion is diagnosed if the difference is more than 5-fold.

In performing the investigation, one also locates the occlusion between two adjacent locations of the occlusion cuff where a change occurs in the quantitative blood supply parameters of the extremity being investigated.

One can similarly diagnose stenosis in other parts of the body, such as arms, hands and fingers of man, the tail of an animal, etc.

In looking for stenosis of arteries, one can investigate not only one extremity, but also a pair of extremities, such as the two legs of a patient. Occlusion cuffs are symmetrically applied to both legs, and the asymmetry of blood supply of both legs is measured and recorded. This makes it possible to compare the effectiveness of blood supply of both legs and cuts down the time it takes to investigate both legs. The same procedure is recommended for a simultaneous investigation of a large set of body parts.

In the case of a preventive checkup of the state of the cardiovascular system of a subject, such as a pilot or a truck driver, it is preferred that variable pressure be symmetrically applied to the brachial artery areas of the right and left shoulders, whereupon one measures and records the quantitative blood supply parameters of both arms and the asymmetry of the supply of blood to the left and right arms. These quantitative parameters are then compared with statistical average ranges of change of such parameters for healthy subjects and patients with known pathologies. If both quantitative blood supply parameters of the subject, or one of them, do not correspond with the statistical average ranges, the inference is a deviation from the norm with regard to the state of the cardiovascular system. It is clear that a more detailed investigation is necessary in order to pinpoint the cause of the deviation.

A patient can check the state of his or her cardiovascular system without the aid of medical personnel, for which purpose he or she must have a household signalling unit in accordance with the invention. Quantitative blood supply parameters can be compared with previously recorded parameters which are considered normal for a given patient. The magnitude and sign of deviations from the normal values tell the patient that he or she must see a doctor. The signalling may be automated.

In looking for atherosclerosis of lower extremities, it is sufficient to simultaneously and symmetrically apply variable pressure to the left and right temporal arteries, the brachial arteries of the left and right legs, and the arteries of the lower third of the shins. This is done by attaching occlusion cuffs in all the above-mentioned areas. In the simplest case, it is enough to measure and record two quantitative parameters, namely, the total blood supply of all the six body parts being investigated, and the relative supply of blood to both legs versus the total supply of blood to both sides of the head. In the manner described above, one established the statistical average ranges of change of these parameters for patients of the same sex and age group suffering from atherosclerosis of the arteries supplying blood to the lower extremities. The first range is 40 to 80 percent of the statistical average range of total blood supply of all the six above-mentioned body parts in healthy subjects. The second range, i.e., the relative blood supply range, is between 0.3 and 2.0. If each quantitative blood supply parameter is within the respective range, the inference is the presence of atherosclerosis of the lower extremities.

By using the same or greater number of quantitative blood supply parameters and the respective statistical average ranges one can accurately diagnose a large number of diseases of the cardiovascular system.

Figure 2:
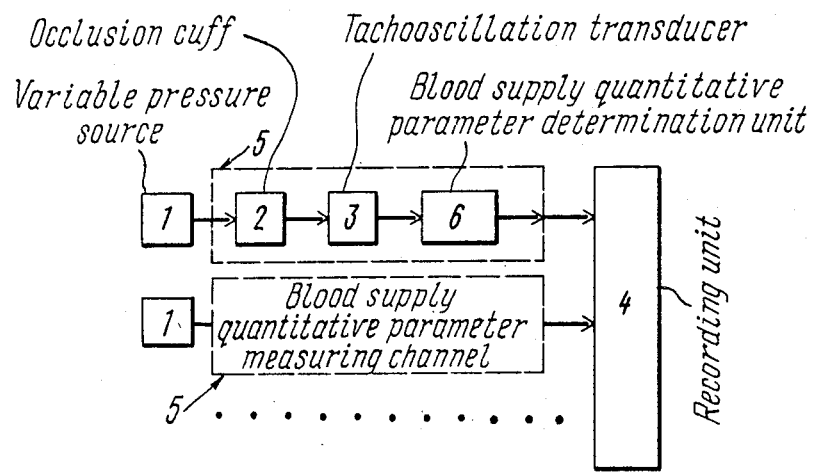
FIG. 2 is a functional diagram of the simplest version of the device according to the invention, intended for investigating at least one part of a body.

The present invention further provides a device for determining the state of the cardiovascular system of living organisms (FIG. 2) which comprises a variable pressure source 1 pneumatically connected to an occlusion cuff 2 and a tachooscillation transducer 3. The device also contains a recording unit 4. It further incorporates at least one blood supply quantitative parameter measuring channel 5 comprising said variable pressure source 1, occlusion cuff 2 and tachooscillation transducer 3, as well as a blood supply quantitative parameter determination unit 6 whose signal input is connected to the output of the tachooscillation transducer 3. The output of the unit 6 serves as the output of the blood supply quantitative parameter measuring channel 5 and is connected to a respective input of the recording unit 4.

The variable pressure source 1 provides linearly rising pneumatic pressure which is applied to the occlusion cuff 2 and through it to a body part being investigated in the area of the blood vessel of that body part. The source 1 may be an air compressor or air bottle with a means for converting constant pneumatic pressure to linearly rising pressure arranged at its outlet. Such a means may be an air throttle and an expansion chamber placed in series and making up a pneumatic integrating circuit. The rate of increase of the pressure P⊓ applied to the occlusion cuff 2 and the degree of its linearity are determined by appropriately selecting the ID of the air throttle, the volume of the expansion chamber, and the level of pressure at the outlet of the air compressor. In FIG. 1a, pressure applied to the occlusion cuff 2 is presented as a function of time. The rate of increase of the pressure P⊓ is normally selected to be equal to 3 to 7 mm of mercury per second; the linearity of this pressure must be at least equal to 5 to 10 percent. To ensure good linearity, the pressure at the outlet of the compressor must be several times higher than the maximum excessive pressure $P_{max}$ applied to the cuff 2 with a view to constructing the blood vessel being investigated. $P_{max}$ is normally 200 to 250 mm of Hg. At the above-mentioned rate of increase of the pressure P⊓, $T_m$, which is the time of applying pressure to the occlusion cuff 2, is 30 to 90 seconds ($T_m = t_2 - t_o$ according to FIG. 1a). $T_m$ is also referred to as the measuring cycle time. With P⊓ increasing at a rate less than 3 mm of Hg per second, the measuring cycle is too long and may be the cause of discomfort on the part of the patient. With P⊓ increasing at a rate higher than 7 or 8 mm of Hg per second, only few tachooscillation half-waves are separated during the measuring cycle, which reduces the accuracy of quantitative determination of the supply of blood to the body part being investigated.

The occlusion cuff 2 serves to apply variable pressure P⊓ directly to the body part being investigated in the area of the blood vessel of that part and convert oscillations of the walls of that vessel, which are due to the pulsation of blood in it, to pulsed fluctuations of pressure in the cuff 2.

The cuff 2 may be a standard cuff of a blood pressure apparatus. If the cuff has only one air supply duct, the input of the tachooscillation transducer 3 is connected to that duct. If the cuff has two independent air supply ducts one of these is connected to the outlet of the variable pressure source 1, while the other is connected to the input of the tachooscillation transducer 3.

In order to have sufficiently high amplitudes of pulsed pressure fluctuations in the cuff 2, which fluctuations are caused by the pulsation of blood, the cuff 2 must be pneumatically isolated from the variable pressure source 1 with regard to pulsed oscillation. For this purpose, an air throttle is installed in the air supply duct of the cuff 2. The internal diameter of the throttle is such that its pneumatic resistance to the flow of air caused by the slowly changing pressure P⊓ applied by the variable pressure source 1 is negligibly small. On the other hand, the pneumatic resistance of the throttle to the air flow caused by relatively faster pulsed fluctuations of pressure in the cuff 2 is of a great magnitude. The air throttle is arranged between the variable pressure source 1 and the input of the tachooscillation transducer 3.

The tachooscillation transducer 3 serves to convert the pulsed pressure fluctuations in the occlusion cuff 2, which are caused by pulsation of blood in the blood vessel of the body part being investigated, to an electric signal corresponding to the first time derivative of the pulsed pressure fluctuations in the cuff 2. This signal is tachooscillation. The tachooscillation transducer 3 may be a standard differentiating pressure sensor like the one used in series-produced arterial oscillographs (cf. Arterial Oscillograph A02-01. Technical Description and Operating Instructions, SKTB Biophyzpribor, Leningrad, 1983). The function of the tachooscillation transducer 3 can also be performed by a standard pressure sensor and a differentiator placed in series with it. Such a system is described in the analogues of the present invention.

The recording unit 4 serves for visual display of quantitative blood supply parameters and/or recording these parameters on paper or other data carrier. The function of the recording unit 4 can be performed by standard pointer-type and digital indicators, visual displays, digital printers, etc.

The blood supply quantitative parameter measuring channel 5 serves to apply variable pressure to the area of the blood vessel of a body part being investigated, separate tachooscillations, and measure the quantitative blood supply parameter of the body part being investigated. It comprises (FIG. 2) the variable pressure source 1, the occlusion cuff 3 and the tachooscillation transducer 3 which are pneumatically interconnected. The channel 5 further incorporates the blood supply quantitative parameter determination unit 6 whose signal input is connected to the output of the tachooscillation transducer 3. The output of the unit 6 is the output of the measuring channel 5.

The blood supply quantitative parameter determination unit 6 serves to measure a quantity corresponding to the sum total of absolute values of the areas of all positive and negative half-waves of separated tachooscillations shown in FIG. 1c. In other words, the unit 6 serves to process the input signal $\phi(t)$ according to the expression (1). It is described in greater detail below (see the embodiment of FIG. 7).

Figure 3:
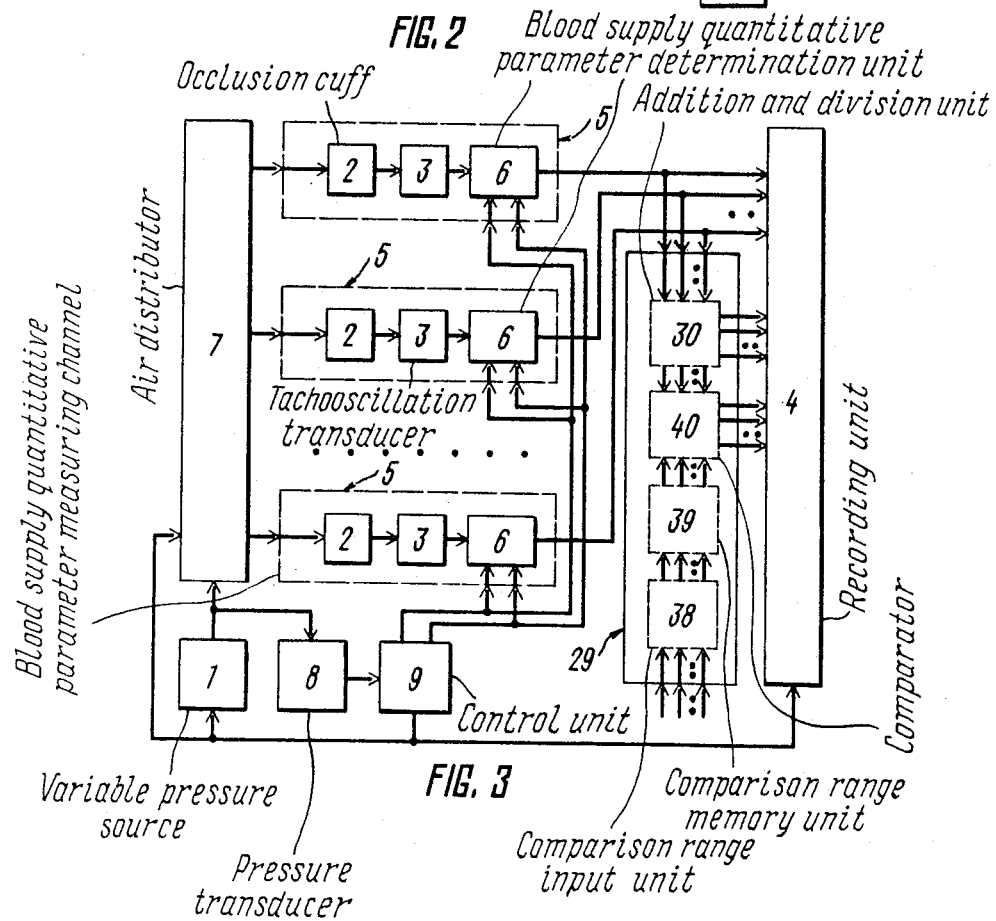
FIG. 3 is a functional diagram of a device according to the invention, intended for investigating two and more body parts.

FIG. 3 shows another embodiment of the device according to the invention for determining the state of the cardiovascular system, which is intended to investigate two or more body parts. The device of FIG. 3 comprises blood supply quantitative parameter measuring channels 5 in a number equal to that of body parts being investigated, each comprising an occlusion cuff 2 pneumatically connected to a tachooscillation transducer 3, and a blood supply quantitative parameter determination unit 6 whose signal input is connected to the output of the tachooscillation transducer 3. The device further incorporates a variable pressure source 1 which is common for all the channels 5, an air distributor 7, a recording unit 4, and a pressure transducer 8 and a control unit 9 which are placed in series. The occlusion cuff 2 of each blood supply quantitative parameter measuring channel 5 is connected to a respective outlet of the air distributor 7 whose inlet is connected to the outlet of the variable pressure source 1 and the input of the pressure transducer 8. The first output of the control unit 9 is connected to respective control inputs of the variable pressure source 1, the air distributor 7 and the recording unit 4. The second and third output of the control unit 9 are respectively connected to the first and second control inputs of each blood supply quantitative parameter determination unit 6 whose output serves as the output of the respective blood supply quantitative parameter measuring channel 5 and is connected to a respective input of the recording unit 4.

The air distributor 7 serves to apply pneumatic pressure generated by the variable pressure source 1, which is common for all the channels 5, to all the occlusion cuffs 2. It also serves for bleeding air from the occlusion cuffs 2 into the atmosphere after pressure in the cuffs 2 reaches a desired level. The air distributor 7 may be of the standard type like the one used in double-channel arterial oscillographs. FIG. 4 presents a simplified pneumoelectric diagram of the air distributor 7 with the occluding cuffs 2 and tachooscillation transducers 3 connected thereto. The air distributor 7 comprises an air duct 10 whose first end is the outlet of the air distributor 7. The second end of the duct 10 is provided with outlets 11. These are outlets of the air distributor 7. Their number is equal to that of the blood supply quantitative parameter measuring channels 5. The air distributor 7 further incorporates an outlet air duct 12 connected to the duct 10 and provided with an electrically controlled air valve 13. An electric control input 14 of the controlled air valve 13 is the control input of the air distributor 7. An air throttle 15 is installed in the air supply duct of each occlusion cuff 2, this is connected to a respective outlet 11 of the air distributor 7. The purpose of the air throttle 15 is provide for pneumatic isolation of the occlusion cuffs 2 from the variable pressure source 1 and from each other in what concerns pulsed pressure fluctuations caused by pulsation of blood in the body parts being investigated.

An alternative manner of pneumatically isolating the occlusion cuffs 2 is dealt with below in the description of the design of the occlusion cuff 2 (see FIGS. 13 and 14).

The pressure transducer 8 serves to convert pneumatic pressure applied by the variable pressure source 1 to the occlusion cuffs 2 to an electric signal proportional to the pressure. This signal is the input signal of the control unit 9. The transducer 8 may be any standard pressure sensor fit for the purpose.

The control unit 9 serves to form a signal for switching on the variable pressure source 1, a signal for closing the controlled air valve 13 of the air distributor 7, and a signal for controlling the recording unit 4 and synchronizing operation of the units 6 of all the blood supply quantitative parameter measuring channels 5. An embodiment of the control unit 9 is presented in FIG. 5. The control unit 9 comprises in a series arrangement a start pulse former 16, a flip-flop 17 and a first AND gate 18. It further incorporates in a series arrangement a comparison circuit 19 with two thresholds, a NOT gate 20, and a second AND gate 21, as well as a start button 22. The output of the comparison circuit 19 with two thresholds is connected to the second inputs of the flip-flop 17 and first AND gate 18. The second input of the second AND gate 21 is connected to the output of the flip-flop 17. The start button 22 is connected to the start pulse former 16. The first input of the comparison circuit 19 with two thresholds is the input of the control unit 9 whose first, second and third outputs are the output of the flip-flop 17 and the outputs of the second and first AND gates 21 and 18, respectively.

Electric potentials $E_1$ and $E_2$, whereby the upper and lower comparison thresholds are set, are applied to the second and third inputs, respectively of the two-threshold comparison circuit 19. The subunits 17 through 21 of the control unit 9 are standard electronic devices. The start pulse former 16 is a standard device whereby the mechanical action of pushing the button 22 is converted to an electric pulse. FIG. 6 is an electric diagram of a simple embodiment of the start pulse former 16 which comprises, in a series arrangement between a source of constant voltage $E_o$ and a ground bus, a first resistor $R_1$ and a capacitor $C_1$, as well as a second resistor $R_2$ whose first lead is grounded, while its second lead, which serves as the output of the start pulse former 16, is connected via the start button 22 to the common point of connection between the first resistor $R_1$ and capacitor $C_1$. It is essential that $R_1 > R_2$.

FIG. 7 is a simplified electric diagram of the unit 6 of the blood supply quantitative parameter measuring channel 5. The blood supply determination unit 6 comprises a lower voltage level limiter 23, an upper voltage level limiter 24, and a two-input integrator 25. The inputs of the limiters 23 and 24 are interconnected and serve as the signal input of the unit 6. The outputs of the limiters 23 and 24 are respectively connected to the first and second signal inputs of the integrator 25 whose first and second control inputs and the output are the first and second control inputs and the output of the blood supply determination unit 6. The integrator 25 is a conventional two-input integrator built around an operational amplifier 26 whose output is the output of the integrator 25. Through the inverting input of the amplifier 26, a negative feedback is provided by means of a $C_2 R_3$ circuit. At the noninverting input of the amplifier 26 there is an integrating $R_4 C_3$ circuit. It is essential that $R_3 = R_4$ and $C_2 = C_3$. One lead of the resistor $R_3$ is connected to the inverting input of the operational amplifier 26. Placed in series with the resistor $R_3$ is a first contact of a first controlled switch 27 whose signal input is the first signal input of the integrator 25. One lead of the resistor $R_4$ is connected to the noninverting input of the operational amplifier 26. Placed in series with the resistor $R_4$ is a second contact of the first controlled switch 27 whose signal input is the second signal input of the integrator 25. Contacts of a second switch 28 are connected in parallel with the capacitors $C_2$ and $C_3$, respectively. The control switches 27 and second controlled switch 28 are standard electronic devices. The control inputs of the switches 27 are respectively connected to the control inputs of the switches 28 and respectively serve as the second and first control inputs of the integrator 25.

According to an alternative embodiment of the invention, the device for determining the state of the cardiovascular system further incorporates a computing unit 29 which comprises an addition and division unit 30 (FIG. 3). The inputs of the addition and division unit 30 are respective inputs of the computing unit 29 and are connected to the outputs of respective blood supply measuring channels 5. The outputs of the addition and division unit 30 are respective outputs of the computing unit 29 and are connected to respective inputs of the recording unit 4. The computing unit 29 serves to perform computation operations while determining total and relative blood supply parameters and establishing the asymmetry of blood supply of body parts being investigated. It also serves to compare measured quantitative parameters with statistical average ranges of change of these parameters for healthy organisms and those with known pathologies. The addition and division unit 30 serves to add and divide quantitative blood supply parameters measured for individual body parts being investigated. It comprises adders and dividers. The number of these and the connections among them are dependent on the number of body parts being investigated, and on the number and type of quantitative blood supply parameters to be determined.

The recording unit 4 incorporates a display or other indication and recording means to indicate and record all blood supply parameters and combinations thereof.

In the case of the investigating two body parts, the addition and division unit 30 of the device according to the invention for determining the state of the cardiovascular system comprises (FIG. 8) a first adder 31 and a first divider 32 which serve to add and divide, respectively, quantitative blood supply parameters of body parts being investigated. The like inputs of said adder 31 and divider 32 are interconnected and serve as the inputs of the addition and division unit 30. The outputs of the adder 31 and divider 32 are the outputs of the addition and division unit 30.

The first adder 31 serves to determine the total supply of blood to both body parts being investigated. The first divider 32 serves to determine the asymmetry of the supply of blood to the two body parts in relation to each other. The calculations are performed according to the expressions (3) and (8), respectively.

The first adder 31 and first divider 32 of the addition and division unit 30 are standard devices. The function of the adder 31 can be performed by conventional analog adders built around operational amplifiers and by digital adders, such as binary ones. The divider 32 may be an analog-digital converter with double integration (cf. Bakhtiarov G. D., Malinin V. V., Shkolin V. P. Analog-Digital Converters/ed. by G. D. Bakhtiarov/, Sovietskoye Radio Publishers, 1980, pp. 167, 168; or Gitis E. I., Piskunov E. A. Analog-Digital Converters, Energoizdat, 1981, pp. 224–228).

If it is necessary to determine the relative supply of blood to the body parts being investigated, the addition and division unit 30 may incroporate two more dividers. Their first inputs are connected to respective inputs of the addition and division unit, whereas their second inputs are connected to the output of the first adder 31. Their outputs are respective outputs of the addition and division unit 30.

In the case of investigating three pair of symmetrical body parts, the addition and division unit 30 of the device according to the invention for determining the state of the cardiovascular system comprises (FIG. 9) a first adder 31 and a first divider 32 for each pair of blood supply measuring channels 5 (see FIG. 3) corresponding to a pair of body parts being investigated. The like inputs of said adder 31 and divider 32 of each pair of channels 5 are interconnected and serve as inputs of the addition and division unit 30. There is also a second adder 33 for said channels 5 corresponding to all the left body parts being investigated. Its inputs are connected to respective inputs of the addition and division unit 30. There is further a third adder 34 for said channels 5 corresponding to all the right body parts being investigated. Its inputs are connected to respective inputs of the addition and division unit 30. There are also a fourth adder 35 and a second divider 36 which is intended to divide total blood supply parameters of all the left and right body parts being investigated. The like inputs of the two latter units are interconnected and respectively connected to the outputs of the second adder 33 and third adder 34.

The first adder 31 and first divider 32 of each pair of blood supply measuring channels 5 serve to calculate the total supply of blood to respective pairs of symmetrical body parts being investigated, as well as the asymmetry of the supply of blood to those parts, the calculation being performed according to the expressions (3) . . . (5) and (8) . . . (10).

The second adder 33 and third adder 34 are to calculate the total supply of blood to all the left and right body parts, respectively, which are being investigated. The calculations are performed according to the expressions (6) and (7).

The fourth adder 35 and second divider 36 serve to calculate the total supply of blood to all the body parts being investigated and the supply of blood to all the left body parts in relation to all the right body parts being investigated. The calculations are performed according to the expressions (2) and (11).

According to another alternative embodiment of the device, which is intended to investigate three pair of symmetrical body parts, the addition and division unit 30 further incorporates (FIG. 9) two third dividers 37 whose first inputs are connected to the output of the first adder 31 for a first pair of blood supply measuring channels 5 corresponding to a certain pair of symmetrical body parts being investigated. The second inputs of the third dividers 37 are respectively connected to the outputs of the first adders 31 of the other blood supply measuring channels 5 corresponding to the other pairs of symmetrical body parts being investigated. The outputs of the third dividers 37 serve as respective outputs of the addition and division unit 30.

The third dividers 37 serve to determine the blood supply of pairs of symmetrical body parts being investigated in relation to the supply of blood to a certain pair of symmetrical body parts. The calculations are performed according to (15).

The number of adders and dividers incorporated in the addition and division unit 30 can be increased or reduced depending on the type of quantitative blood supply parameters used in a diagnosis of a disease or examination of a patient. If it is necessary, for example, to determine relative supply of blood to the body parts being investigated, or relative supply of blood to certain combinations of body parts, such as pairs of symmetrical body parts, and all left and right body parts being investigated, it is sufficient that additional dividers be incorporated in the addition and division unit 30. The first inputs of the additional dividers are to be connected to respective inputs of the addition and division unit 30, to the outputs of the first adders 31 for respective pairs of the blood supply measuring channels 5, and to the outputs of the second adder 33 and third adder 34. The second inputs of the additional dividers are to be connected to the output of the fourth adder 35. The outputs of the additional dividers are to be connected to respective outputs of the addition and division unit 30.

According to another alternative embodiment of the device of this invention, the computing unit 29 (FIGS. 3 and 8) additionally incorporates in a series arrangement a comparison range input unit 38, a comparison range memory unit 39 and a comparator 40 whose other inputs are connected to respective outputs of the addition and division unit 30. The inputs of the comparison range input unit 38 serve as respective inputs of the computing unit 29. The outputs of the comparator 40 serve as respective outputs of the computing unit 29.

The comparison range input unit 39 serves to enter into the comparison range memory unit 39 a system of numbers setting the upper and lower boundaries of the statistical average ranges of change of quantitative parameters for healthy subjects and patients with known pathologies. The comparison range memory unit 39 serves for storing these numbers. The units 38 and 39 are standard units of present-day computing devices.

The comparator 40 serves to compare measured parameters of blood supply of body parts being investigated or combinations thereof with ranges of change of these parameters for healthy subjects and patients with known pathologies, and produce output signals corresponding to the results of the comparison.

The recording unit 4 is provided with an additional display means or other indication and recording means which make it possible to indicate and record the results of a comparison of measured quantitative blood supply parameters with statistical average ranges of change of these parameters for healthy subjects and patients with known pathologies.

In the case of investigating two body parts, the comparator 40 (FIG. 8) comprises first and second comparison circuits 41 and 42 intended to compare data with a first comparison range and a second comparison range, respectively, and a two-input NAND gate 43. The inputs of the NAND gate 43 are respectively connected to the outputs of the comparison circuits 41 and 42. The signal input of the comparison circuit 41 is a respective input of the comparator 40 and is connected to the output of the first adder 31 of the addition and division unit 30. The signal input of the comparison circuit 42 serves as a respective input of the comparator 40 and is connected to the output of the first divider 32 of the addition and division unit 30. The first and second threshold inputs of the comparison circuits 41 and 42 serve as respective inputs of the comparator 40 and are connected to respective outputs of the comparison range memory unit 39. The output of the NAND gate 43 serves as the output of the comparator 40 and a respective output of the computing unit 29.

The first comparison circuit 41 serves to compare the total supply of blood to both body parts being investigated with the statistical average range of change of this quantitative parameter for the same body parts of healthy subjects of the same sex and age group. The second comparison circuit 42 serves to compare the asymmetry of the supply of blood to one body part in relation to the supply of blood to the other body part being investigated with the statistical average range of change of this parameter for the same body parts of helathy subjects of the same sex and age group. The comparison circuits 41 and 42 are standard electronic devices.

The NAND gate 43 serves for logical integration of the output signals of the comparison circuits 41 and 42.

In increasing the number of quantitative blood supply parameters, the number of comparison circuits, as well as the number and composition of the logic elements of the comparator 40 have to be increased accordingly. The connections of these elements are determined by the performance algorithm of the comparator 40 and the addition and division unit 30.

According to a still another embodiment of the invention, the device for determining the state of the cardiovascular system incorporates a tachooscillation separation time measuring unit 44. In this case each blood supply measuring channel 5 incorporates a fourth divider 45 for dividing a measured quantitative blood supply parameter by a measured duration of the separation of tachooscillations. The first input of the fourth divider 45 is connected to the output of the blood supply determination unit 6. The second input of the fourth divider 45 is connected to the output of the tachooscillation separation time measuring unit 44. The output of the fourth divider 45 is the output of the blood supply measuring channel 5. The input of the tachooscillation separation time measuring unit 44 is connected to the third output of the control unit 9.

The unit 44 serves to measure the time during which tachooscillations are separated. It may either be a constant potential analog integrator or a triggered count pulse oscillator with a pulse counter connected in series with it. In both cases the output signal of these devices is proportional to the time during which tachooscillations are separated.

The fourth divider 45 serves to divide a measured quantitative blood supply parameter by a measured duration of the separation of tachooscillations. From the viewpoint of design, it may be identical with other dividers incorporated in the addition and division unit 30.

Figure 11:
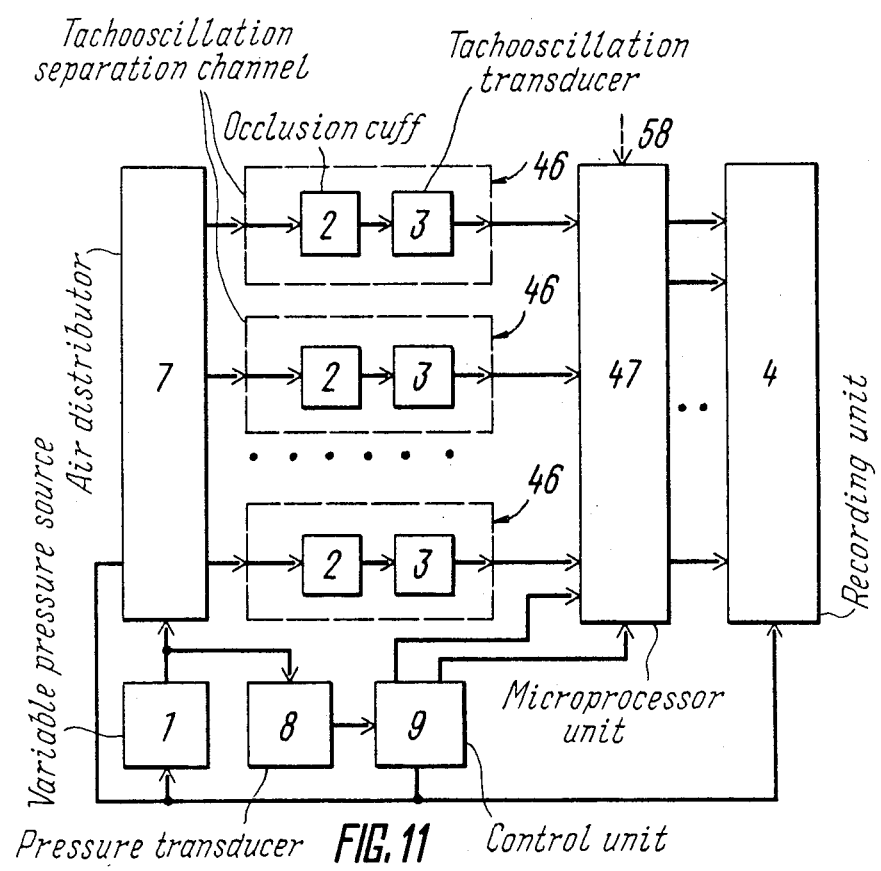
FIG. 11 is a functional diagram of another alternative embodiment of the device according to the invention, provided with a microprocessor for tachooscillation processing.

Another alternative embodiment of the device according to the invention for determining the state of the cardiovascular system is shown in FIG. 11. It comprises the variable pressure source 1, the air distributor 7, and tachooscillation separation channels 46 in a number equal to that of body parts being investigated. Each of the channels 46 comprises the occluding cuff 2 and tachooscillation transducer 3 which are pneumatically interconnected, the output of the tachooscillation transducer 3 being the output of the tachooscillation separation channel 46. The device further contains the recording unit 4, a microprocessor unit 47 which serves to process tachooscillations, its outputs being connected to respective inputs of the recording unit 4, and the pressure transducer 8 and control unit 9 that are placed in series. The occlusion cuff 2 of each tachooscillation separation channel 46 is connected to a respective outlet of the air distributor 7 whose inlet is connected to the outlet of the variable pressure source 1 and the input of the pressure transducer 8. The first output of the control unit 9 is connected to respective control inputs of the variable pressure source 1, air distributor 7 and recording unit 4. The second and third outputs of the control unit 9 are respectively connected to the control and signal inputs of the microprocessor unit 47 whose other signal inputs are connected to the outputs of the respective tachooscillation separation channels 46.

The functions of the units 1, 2, 3, 4, 7, 8 and 9 are described above. Unlike the blood supply quantitative parameter measuring channel 5, the tachooscillation separation channel 46 is only intended to separate tachooscillations, wherefore it only comprises an occlusion cuff 2 and a tachooscillation transducer 3.

Figure 12:
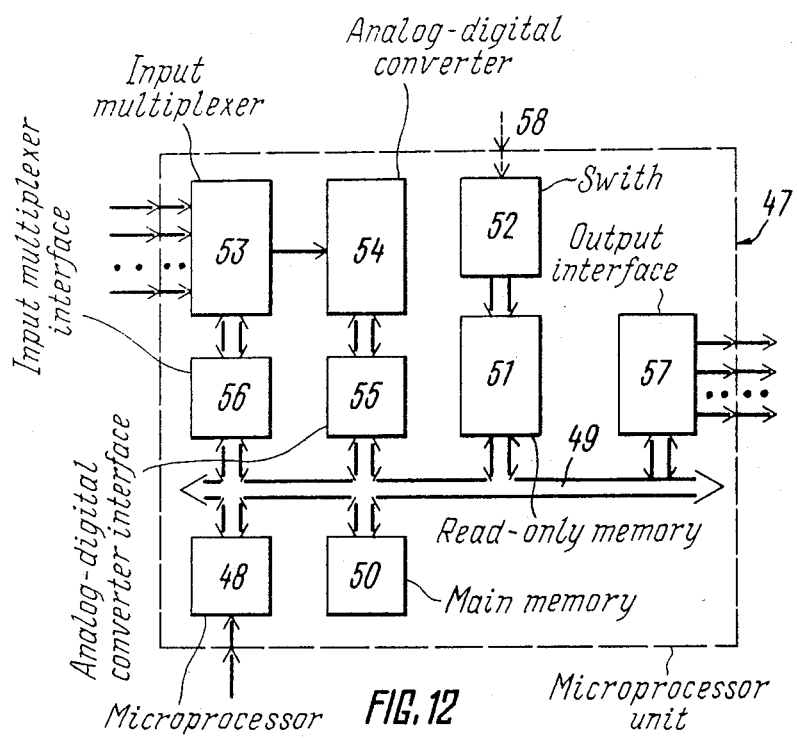
FIG. 12 is a functional diagram of an alternative embodiment of the tachooscillation processing unit (the microprocessor)

The microprocessor unit 47 is intended to calculate values corresponding to sums of absolute areas of all positive and negative half-waves of separated tachooscillations. In other words, it is intended to determine quantitative blood supply parameters, relate them to the tachooscillation separation time, calculate quantitative blood supply parameters of combinations of body parts being investigated, compare the quantitative blood supply parameters of a patient with statistical average ranges of change of these parameters for healthy subjects and patients with known pathologies, and use the results of the comparison to send corresponding signals to the recording unit 4. FIG. 12 presents a functional diagram of one of possible embodiments of the microprocessor unit 47.

The microprocessor unit 47 comprises a microprocessor 48 with an internal clock pulse generator connected to a common bus 49, a main memory 50 and a permanent (ROM) read-only memory 51 which are connected to the common bus 49, and a switch 52 of the ROM 51 placed in series with the latter. The microprocessor unit 47 further incorporates in a series arrangement an input multiplexer 53 whose inputs are respective signal inputs of the microprocessor unit 47, an analog-digital converter 54 and an analog-digital converter interface 55 connected to the common bus 49, an input multiplexer interface 56 of the input siwtch connected to the common bus 49 and the input switch 53, and an output interface 57 connected to the common bus 49. The outputs of the output interface 57 serve as the outputs of the microprocessor unit 47. If separate buses are used, the common bus 49 incorporates all of them, such as the data bus, address bus, etc.

The control electric input of the microprocessor 48 is the control input of the microprocessor unit 47. A mechanical input 58 of the switch 52 of the ROM 51 is the program switching input of the microprocessor unit 47.

All the units and devices incorporated in the microprocessor unit 47 are standard electronic units and devices.

Figure 13:
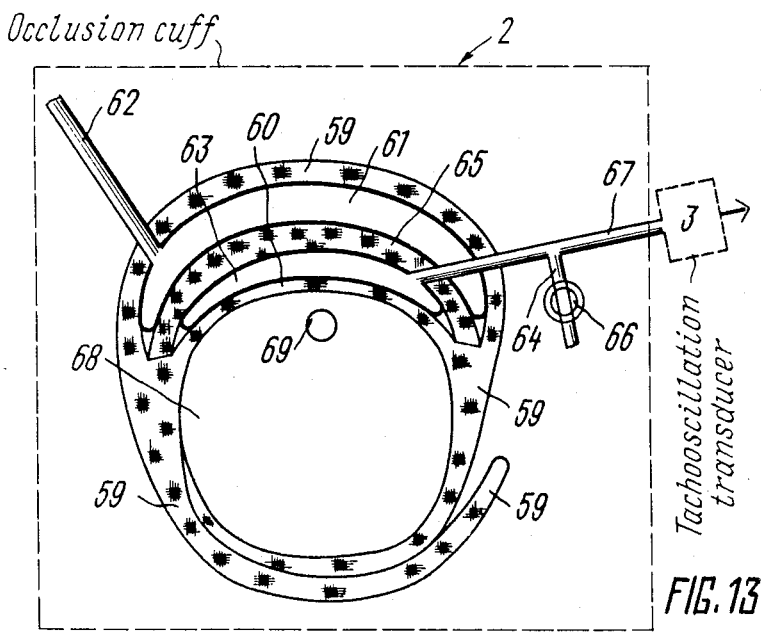
FIG. 13 is a cross-sectional view of the occlusion cuff of the device in accordance with the invention.
Figure 14:
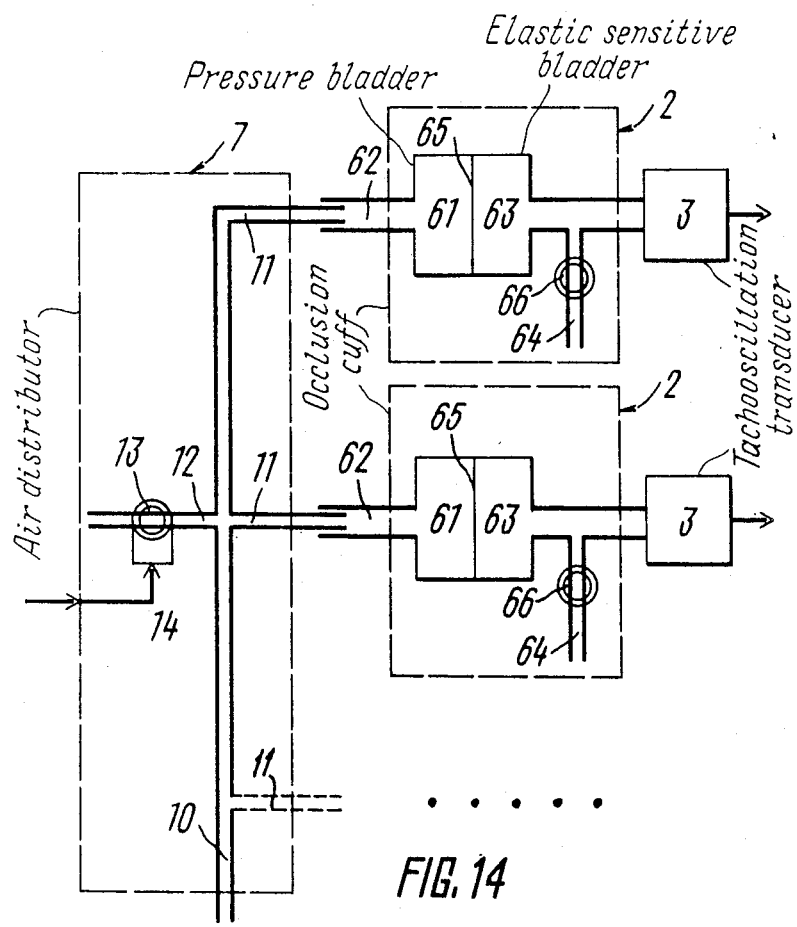
FIG. 14 is a functional pneumatic diagram of the air distributor with occlusion cuffs in accordance with the invention.

In a still another embodiment of the present invention, use is made of occluding cuffs 2 shown in FIG. 13. FIG. 14 is a simplified diagram showing the pneumatic connection of th occluding cuffs of FIG. 13 to the air distributor 7 and the tachooscillation transducer 3.

FIG. 13 shows an occluding cuff 2 in cross-section. The occlusion cuff 2 comprises a sheath 59 of a non-stretchable material, such as tarpaulin, with a means for attaching the cuff 2 to a patient's body (said means are not shown in FIGS. 13 and 14). Such a means may be a fastener, a hook and eye, a Velcro-type connection, etc. Attached to the internal side of the sheath 59, which faces the patient's body, is an elastic pocket 60 preferably of thin silk. The pocket 60 of the sheath 59 of the cuff 2 accommodates a pressure bladder 61 of thin rubber provided with an air supply duct 62 whereby it directly communicates with a respective outlet of the air distributor 7. Between the pressure bladder 61 and the wall of the pocket 60 next to the patient's body there is an elastic sensitive bladder 63 of thin rubber, which is provided with an air supply duct 64.

The pressure bladder 61 is separated from the sensitive bladder 63 by a flexible partition 65 of the pocket 60. The air supply duct 64 of the sensitive bladder 63 is provided with a shut-off valve 66. An input duct 67 of the tachooscillation transducer 3 is connected to the air supply duct 64 between the valve 66 and the sensitive bladder 63. Thus the input 67 of the tachooscillation transducer 3 is directly connected to the sensitive bladder 63. As is seen from FIG. 13, the occlusion cuff 2 is so arranged on the patient's body 68 that the sensitive bladder 63 is at a minimum distance from a blood vessel 69 of the body part being investigated.

The flexible partition 65 is of a material with a considerable internal friction caused by deformations, such as bending and stretching. Tarpaulin is best suited for the purpose. By selecting the thickness and material of the flexible partition 65 with an appropriate specific internal friction coefficient, one ensures a desired pneumatic resistance of the flexible partition 65 of each cuff 2.

If the device according to the invention, use can be made of standard cuffs, such as those of arterial blood pressure apparatus. Cuffs of this type are used in the embodiments of FIGS. 2 and 4. Such a cuff 2 comprises a sheath 59 with a elastic pocket 60 and with a means for attaching the cuff to the patient's body. It further includes a pressure bladder 61 accommodated in the pocket 60 of the sheath 59 and provided with an air supply duct 62. The pressure bladder 61 of each cuff 2 is directly connected to the output 67 of the tachooscillation unit 3. Via the isolating air throttle 15, it is connected to the outlet 11 of the air distributor 7 (FIG. 4) or the outlet of the variable pressure source 1 (see the description of the embodiment of FIG. 2). The air throttle 15 is installed in the air supply duct 62 between the input 67 of the tachooscillation transducer 3 and the respective outlet 11 of the air distributor 7 (FIG. 4).

The latter version of the cuff 2 is disadvantageous in a low accuracy of quantitative blood supply determination due to uncontrolled changes in the pneumatic resistance of the air throttle 15 which may be partially clogged with dust, talcum powder and other foreign matter. The reliability of a device for determining the state of the cardiovascular system incorporating such cuffs 2 is inadequate, because a complete clogging of the throttle 15 leads to a failure of the respective blood supply quantitative parameter measuring channel 5.

The above disadvantages of the standard cuff are still more manifest in simultaneously investigating several body parts with the use of a corresponding number of cuffs 2. The more cuffs 2 one uses, the greater the probability of one or more air throttles 15 getting clogged. The differences in the pneumatic resistance of the throttles 15 and uncontrolled changes of that resistance lead to a situation when pressure levels in the pressure bladders 61 of the cuffs 2 differ considerably and are subject to uncontrolled changes with respect to one another and to the pattern of change in the pressure applied to the cuffs 2 (i.e., the pressure at the outlets 11 of the air distributor 7). The above factors distort quantitative blood supply measurements, affect the accuracy of evaluating the state of the cardiovascular system, and may lead to diagnostic errors.

These factors act as follows. The air throttle—pressure bladder system is equivalent to an integrating circuit of the first order. This means that following an application to the air throttle 15 of a linearly rising pressure $P\sqcap(t) = kt$, the pressure in the pneumatic bag 61 changes like this:

$$P\sqcap\sqcap(t) = kt - K\tau[1 - \exp(-t/\tau)],$$

where
k is a coefficient characterizing the rate of change of the inlet pressure;
t is running time; and
$\tau$ is the time constant of the air throttle—pressure bladder system, which is the product of the pneumatic resistance of the air throttle 15 by the internal volume of the pressure bladder 61.

It follows from the above equation that any change of the time constant $\tau$, which may be due, for example, to a change of the pneumatic resistance of the air throttle 15 because of its getting clogged, may alter the pattern of change of the pressure applied to the body part being investigated. If N cuffs 2 are used, the time constants $\tau_i$ (where i=1, 2, 2, ... N) of the cuffs 2 may vary considerably due to a different degree of clogging of the air throttles 15 and because of variations of the channel diameters of the air throttles 15, considering that these diameters are in the order of a few fractions of a millimeter and the pneumatic resistance of the air throttles is inversely proportional to the channel diameter raised to the fourth power. The above factors account for considerable variations in the pattern of change of the pressure in the pressure bladders 61 of the cuffs 2 and reduce the accuracy of measuring quantitative blood supply parameters of body parts being investigated. The result is an inadequate accuracy of evaluating the state of the cardiovascular system.

In the embodiment of the occluding cuff 2 according to the present invention (FIGS. 13 and 14), use is made of the flexible partition 65 between the sensitive bladder 63 and the pressure bladder 61. The purpose of the partition 65 is to isolate the sensitive bladder 63 of the cuffs 2 from the variable pressure source 1 and from one another in what concerns pulsed pressure fluctuations due to the pulsation of blood in the body parts being investigated. The flexible partition 65 is advantageous in that its pneumatic resistance is constant throughout the service life of the device. The flexible partition—sensitive bladder system is also equivalent to an integrating circuit of the first order. The pressure in the sensitive bladder 65 varies according to the expression $P\sqcap\sqcap(t)$ with the time constant $\tau$ being the product of the pneumatic resistance of the flexible partition 65 by the internal volume of the sensitive bladder 63. Thus from the viewpoint of its function, this system is equivalent to the air throttle—pressure bladder system of the standard cuff, but has a number of advantages over the latter. First, the system according to the invention never gets clogged, which rules out uncontrolled changes of the time constants of the cuffs 2 and increases the reliability of the whole device for determining the state of the cardiovascular system. Second, the system according to the invention makes the time constants $\tau_i$ of all the cuffs 2 equal despite the different sizes of the cuffs 2 meant to be attached to different parts of the body, such as the head or the hip. This is achieved by appropriately selecting the material and the size of the flexible partitions 65, i.e., by ensuring a correspondence between the pneumatic resistance of each flexible partition 65 and the volume of the respective sensitive bladder 63.

In the occlusion cuff 2 according to the invention (FIGS. 13 and 14), the input 67 of the tachooscillation transducer 3 is in direct communication with the internal cavity of the sensitive bladder 63. As a result, the tachooscillation transducer 3 fully separates tachooscillations from pulsed pressure fluctuations in the sensitive bladder 63.

Due to the foregoing advantages of the occlusion cuff 2 according to the invention (FIGS. 13 and 14), the pattern of change of pressure is identical in the sensitive bladder 63 of all the cuffs 2, which accounts for a consistently high accuracy of measuring quantitative blood supply parameters and a high accuracy of determining the state of the cardiovascular system of a patient.

The device according to the invention for determining the state of the cardiovascular system operates as follows.

In investigating at least one body part of a living organism, such as a human being or a warm-blooded animal, the ocluding cuff 2 of a respective blood supply quantitative parameter measuring channel 5 (FIG. 2) is attached to the body part to be investigated. It is attached, for example, to the shoulder in the area of its brachial artery, whereupon it is connected to the variable pressure source 1. The connection is through the air throttle 15 if a standard cuff 2 is used. In the case of using a cuff 2 according to the invention, which is shown in FIG. 13, the pressure bladder 61 of the cuff 2 is connected to the variable pressure source 1 by means of the air supply duct 62. In this case the function of the air throttle 15 is performed by the flexible partition 65. Through the flexible partition 65, the pressure applied by the variable pressure source 1 is transmitted to the sensitive bladder 63 of the cuff 2.

The pressure $P\sqcap$ applied to the cuff 2 is then varied. It may be varied linearly, for example, being raised at a rate of V=3 ... 7 mm of Hg per second, as is shown in FIG. 1a. As the pressure reaches the value of $P_{min}$, which normally is below 50 mm of Hg, the cuff 2 constricts the entire body part 68 (FIG. 13) being investigated. As a result, variable pressure is applied to the body part 68 in the area of its blood vessel 69 under the cuff 2. Beginning from this instant $t_1$ (see FIG. 1a), the full pneumatic pressure in the sensitive bladder 63 of the cuff 2, i.e., $P_m$ (see FIG. 1b), is a sum total of the linearly rising pressure of the variable pressure source 1 and pulsed pressure fluctuations caused by the oscillations of the walls of the blood vessel 69 due to the pulsation of blood in that vessel 69. The elastic sheath of the sensitive bladder 63 and the wall of the pocket 60 of the cuff 2 offer a slight pneumatic resistance to the pulsed fluctuations. At the same time the sensitive bladder 63 is completely isolated, in what concerns the pulsed fluctuations, from the pressure bladder 61 of the cuff 2 and, consequently, from the variable pressure source 1, bearing in mind that the pneumatic pressure of the partition 65 is greater by several times than the total pneumatic resistance of the wall of the sensitive bladder 63 and the wall of the pocket 60 of the cuff 2.

The tachooscillation transducer 3 converts the pulsed pressure fluctuations to an electric signal corresponding to the first time derivative of said pulsed pressure fluctuations. The output signal of the tachooscillation transducer 3 is roughly presented in FIG. 1c. The signal in question covers a period of time $T=t_2-t_1$, where $t_2$ is an instant when the pressure applied by the variable pressure source 1 to the occluding cuff 2 reaches a maximum level $P_{max}$ (FIG. 1a). At $P_{max}$, tachooscillations are practically nonexistent, because the cuff 2 fully constricts the blood vessel of the body part being investigated. As $P\sqcap$ reaches the level of $P_{max}=200 \ldots 250$ mm of Hg, the variable pressure source 1 is disconnected and the pressure in the cuff 2 is rapidly reduced to the original level. This is normally done by communicating the cuff 2 with the atmosphere and allowing the excessive air to escape. The instant when the variable pressure source is disconnected and the cuff 2 is communicated with the atmosphere is determined either with the aid of an auxiliary pressure sensor installed at the outlet of the source 1 or with the aid of a timer switched on at the start of applying variable pressure $P\sqcap$ to the cuff 2. In the latter case the variable pressure source 1 is disconnected after a period of time $T_m=P_{max}/V=t_2-t_o$ (see FIG. 1a). For example, $T_m=40$ sec at $P_{max}=200$ mm of Hg and the rate of increase of $P\sqcap$, i.e., V=5 mm of Hg per second.

The output signal of the tachooscillation unit 3 is applied to the input of the blood supply quantitative parameter determination unit 6. The quantitative blood supply parameter of a given body part determined by the unit 6 corresponds to a sum total of the absolute areas of all positive and negative half-waves of the tachooscillations.

As a result, at an instant $t_2$ a signal is produced at the output of the blood supply determination unit 6, whose value is determined by the expression (1).

This output signal is applied to the recording unit 4 which either displays it as a number on a digital indicator, or records or prints it on paper or other data carrier. The signal can be both indicated and recorded (printed), whereupon it can be entered in the case history.

The value thus recorded is a new parameter which was not used in the past for the determination of the state of the cardiovascular system. In order to make an effective use of this parameter, one has to known its distribution in healthy organisms and organisms with known pathologies of the cardiovascular system. One also has to known the statistical average ranges of change of this parameter in these organisms with due regard for the sex, age group, and species, such as man, ape, dog, etc. By comparing the measured blood supply parameter with a statistical average range of its change, it is possible to determine the state of the patient's cardiovascular system.

The statistical average ranges are established according to the rules of mathematical statistics by processing the results of similar investigation of the same body parts of a considerable number of healthy organisms and those with known pathologies.

In the simplest case discussed above, the comparison of the measured quantitative blood supply parameter S of the body part being investigated with the statistical average ranges of change of this parameter is done by the physician.

In investigating two or more body parts, such as two arms or two legs of a human being, occlusion cuffs 2 of the respective blood supply quantitative parameter measuring channels 5 (FIG. 3) are attached to all the body parts being investigated in the area of their blood vessels. For example, cuffs 2 are attached in the area of the brachial artery of the arm and in the area of the shin artery. The occlusion cuffs 2 are then connected to the respective outlets 11 of the air distributor 7 (FIG. 4), whereupon the start button 22 of the control unit 9 (FIGS. 5 and 6) is pushed. The capacitor $C_1$, charged through the resistor $R_1$ to a voltage $E_o$ supplied by a constant voltage source, discharges through the resistor $R_2$ whose resistance is much lower than that of the resistor $R_1$. As a result of the discharge, a sharp start pulse shown in FIG. 1d is produced across the resistor $R_2$. This pulse changes the state of the flip-flop 17 at whose output a rectangular change of voltage pulse shown in FIG. 1e is produced. The flip-flop 17 triggers off the variable pressure source 1, closes the controlled air valve 13 of the air distributor 7 (FIG. 4), and gets the recording unit 4 ready for operation. The variable pressure source 1 generates linearly increasing pneumatic pressure P (FIG. 1a) which is simultaneously applied through the air distributor 7 and air throttles 15 (if standard cuffs 2 shown in FIGS. 3 and 4 are used) to the occlusion cuffs 2 which operate as described above.

If use is made of the occluding cuffs 2 shown in FIG. 13, the pressure bladder 61 of each cuff 2 is directly connected by the air supply duct 62 to the respective outlet 11 of the air distributor 7, so pressure generated by the source 1 is transmitted without being changed to the pressure bladder 61 of all the cuffs 2. Through the flexible partitions 65, pressure is transmitted to the sensitive bladders 63 of all the cuffs 2 and is thus applied to all the body parts being investigated. The pressure tranducer 8 converts the variable pressure $P_\sqcap$ applied to the cuffs 2 to an electric signal applied to the first (signal) input of the two-threshold comparison circuit 19 (FIG. 5). The lower threshold is set by the potential $E_1$ and corresponds to a minimum pressure $P_{min}$ in the cuffs 2 (FIG. 1a). As the $P_{min}$ level is reached, tachooscillations of a discernible amplitude are detected at the output of the tachooscillation transducer 3. The upper threshold of the comparison circuit 19 is set by the potential $E_2$ and corresponds to a maximum pressure $P_{max}$ in the occlusion cuff 2. The shape of the output voltage of the two-threshold comparison circuit 19 is shown in FIG. 1f. The output signal of the two-threshold comparison circuit 19 is applied to the first AND gate 18 and via the NOT gate 20 to the second AND gate 21. The output signal of the flip-flop 17 is applied to the other inputs of the AND gates 18 and 21. The output signal of the second AND gate 21 is shown in FIG. 1g. The output signal of the first AND gate 18 is shown in FIG. 1h. The output signal of the second AND gate 21, which is a rectangular pulse, is applied from the second output of the control unit 9 to the first control input of each blood supply quantitative parameter determination unit 6.

The control pulse closes the second controlled switches 28 of the two-input integrator 25 (FIG. 7). As a result, the integrator 25 is brought to its initial operating state, i.e., zeroized, because its capacitors $C_2$ and $C_3$ rapidly discharge to zero voltage through the closed switches 28 with their low-value resistors.

The output signal of the first AND gate is a rectangular pulse whose duration is equal to the tachooscillation separation time. This pulse is applied from the third output of the control unit 9 to the second control input of each blood supply determination unit 6 and brings the controlled switches 27 from a state in which both signal inputs of the integrator 25 are grounded to a state in which the signal inputs of the integrator 25 are connected to the outputs of the limiters 23 and 24, respectively.

As the pneumatic pressure $P_\sqcap$ applied to the occluding cuffs increases, tachooscillations are produced at the output of each tachooscillation transducer 3. Tachooscillations are shown in FIG. 1c. In each blood supply quantitative parameter measuring channel 5, tachooscillations are applied to the blood supply quantitative parameter determination unit 6. In this unit (FIG. 7), tachooscillations are first applied to interconnected inputs of the lower level limiter 23 and upper level limiter 24. Only positive half-waves of the separated tachooscillations are applied via the lower level limiter 23 to the first signal input of the integrator 25, and only negative half-waves of the separated tachooscillations are applied via the upper level limiter 24 to the second signal input of the integrator 25. The integrator 25 produces a time integral on the basis of the difference of voltages at its first and second signal inputs, so at an instant $t_2$ (FIG. 1a), when the pneumatic pressure $P_\sqcap$ applied to the occlusion cuffs 2 reaches a $P_{max}$ level, the output voltage of the integrator 25 is equal to the sum total of the absolute areas of all positive and negative half-waves of the separated tachooscillations. This means that the output signal of the integrator 25 corresponds to the quantitative blood supply parameter S which is being sought and which is determined by the expression (1). At this instant, the flip-flop 17 is reset by the first negative output voltage pulse of the two-threshold comparison circuit 19. As a result, the variable pressure source 1 is switched off, the controlled air valve 13 of the air distributor 7 opens, and the controlled switches 27 ground both signal inputs of the integrator 25 of the blood supply determination unit 6, whereby zero potential is produced at said inputs of the integrator 25. The excessive air rapidly escapes from the cuffs 2 through the open valve 13, whereby the pressure in the cuffs 2 is reduced to zero in relation to the atmospheric pressure (FIG. 1a). The output voltage of each integrator 25 is equal to the measured quantitative blood supply parameter $S_i$, where i=1, 2, ..., N, and N is the number of body parts being investigated simultaneously. The quantitative blood supply parameters thus measured are recorded by the recording unit 4, i.e., at the end of the control pulse applied from the first output of the control unit 9 they are either displayed on visual indicators, or printed on paper cards, or recorded in some other manner.

Apart from using quantitative blood supply parameters of certain body parts being investigated, a diagnostician can also use quantitative blood supply parameters of certain combinations of body parts, such as the total supply of blood to all the body parts being investigated, the asymmetry of the supply of blood to pairs of symmetrical body parts, their relative blood supply and other parameters described in the present disclosure. All these parameters are automatically calculated by the addition and division unit 30 incorporated in the computing unit 29 of the device according to the invention for determining the state of the cardiovascular system (see FIG. 3). The above-mentioned parameters are indicated and recorded by the recording unit 4. In doing so, the operation of the units 1 through 28 of the device according to the invention is similar to what is described above. The operation and preferred embodiments of the computing unit 29 and addition and division unit 30 are described below.

In investigating two body parts, such as the left and right arms, the addition and division unit 30 incorporated in the device shown in FIG. 8 calculates the total supply of blood to both arms and the asymmetry of their blood supply. The former parameter is calculated by the first adder 31. Appropriate data are applied to its inputs from the inputs of the addition and division unit 30. The latter parameter is calculated by the first divider 32 which serves to divide the quantitative blood supply parameters of said body parts being investigated, which are applied to its inputs from the inputs of the addition and division unit 30. The data on total blood supply of the two arms and the assymmetry of their blood supply are sent to the outputs of the addition and division unit 30 and recorded by the recording unit 4.

In the case of investigating three pair of symmetrical body parts, the addition and division unit 30 (FIG. 9) calculates the following quantitative blood supply parameters of the foregoing combination of body parts.

The first adder 31 for each pair of blood supply quantitative parameter measuring channels 5 (FIG. 3) corresponding to a pair of body parts being investigated calculates the quantitative parameter of the total supply of blood to the respective pair of symmetrical body parts. For example, in investigating the left and right sides of the head, left and right arms, and left and right legs with the aid of six blood supply quantitative parameter measuring channels, six quantitative blood supply parameters are determined, i.e., $S_1$, $S_2$, $S_3$, $S_4$, $S_5$, $S_6$, corresponding in this order to the six body parts mentioned above. At the outputs of the respective three first adders 31 there are produced signals corresponding to the quantitative parameters of the total blood supply of the head: $S_{12}$, both arms: $S_{34}$, and both legs: $S_{56}$. The parameters are derived from the equations (3) ... (5).

The first divider 32 of each pair of the channels 5 corresponding to a pair of symmetrical body parts being investigated calculates the quantitative parameter of the asymmetry of blood supply of a respective pair of symmetrical body parts being investigated. In the present example, at the outputs of the three dividers 32 there are produced signals corresponding to the above-mentioned quantitative parameters derived from the equations (8) ... (10), i.e., $A_{12}$, $A_{34}$, and $A_{56}$.

The second adder 33 for said channels 5 corresponding to all the left body parts being investigated calculates the quantitative parameter of the total blood supply of all the left body parts and produces a quantitative parameter $S_{135}$ derived from (6).

The third adder 34 for said channels 5 corresponding to all the right body parts being investigated calculates the quantitative parameter of the total supply of blood to all the right body parts and produces a quantitative parameter $S_{246}$ derived from (7).

The fourth adder 35, which serves to calculate the quantitative parameter of the total blood supply of all the left and right body parts being investigated, determines $S_\Sigma$ which is derived from (2).

The second divider 36, which serves to divide quantitative parameters characterizing the total blood supply of all the left and right body parts being investigated, calculates the quantitative parameter of the blood supply of all the left body parts in relation to that of all the right body parts, i.e., $A_\Sigma$ which is derived from (11).

Figure 9:
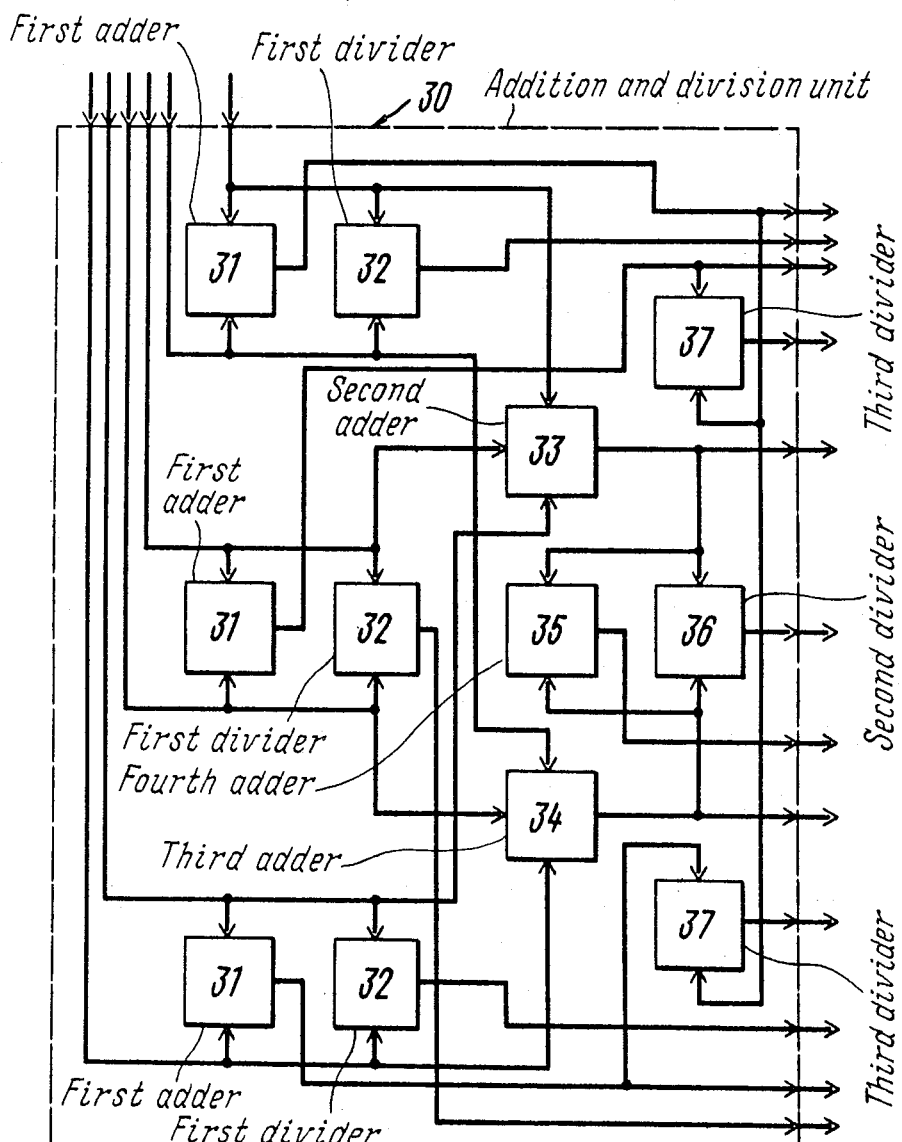
FIG. 9 is a functional diagram of the addition and division unit of a device according to the invention intended for the investigation of three pair of symmetrical body parts.
Figure 10:
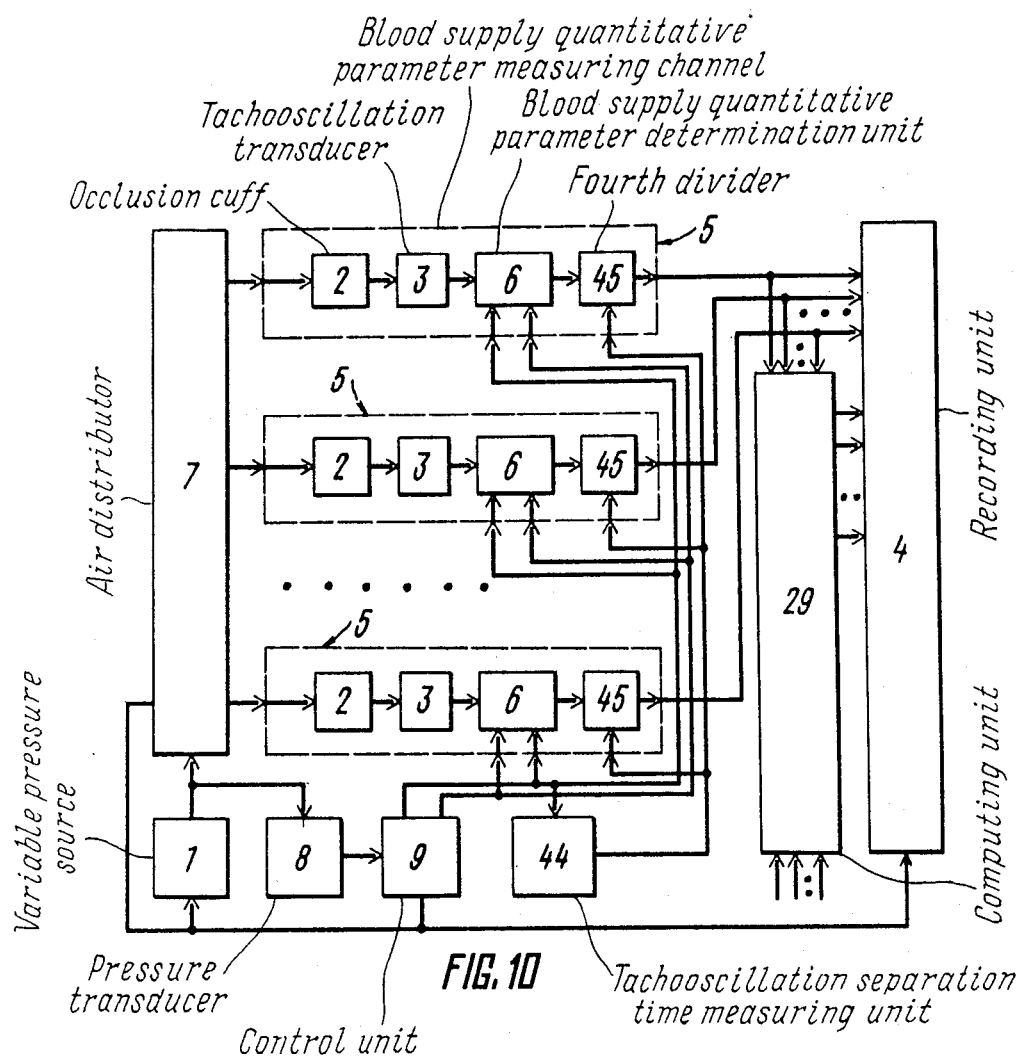
FIG. 10 is a functional diagram of an alternative version of the device according to the invention for determining the state of the cardiovascular system.

The conversion of signals which serve to produce all the foregoing parameters is clear from a consideration of FIG. 9.

According to another embodiment of the invention, the addition and division unit 30 (FIG. 9) also the quantitative parameters of the relative blood supply of pairs of symmetrical body parts. For three pair of channels 5 (see also FIG. 3) corresponding to three pair of symmetrical body parts being investigated, these parameters are calculated by the two third dividers 37. To the first input of each of said dividers 37, a signal is applied corresponding to the quantitative parameter of the total blood supply of one certain pair of symmetrical body parts. The quantitative parameters of the relative blood supply of the other pairs of symmetrical body parts is calculated with reference to this parameter. The signal is applied from the output of the first adder 31 for one pair of said channels 5 corresponding to a certain pair of symmetrical body parts being investigated. To the second inputs of the third dividers 37 there are applied signals from the outputs of the first adders 31 for the other two pair of channels 5 corresponding to the two other pair of symmetrical body parts being investigated.

Thus the two third dividers 37 calculate $B_{34}$ and $B_{56}$, respectively, which parameters are derived from (15).

In a still another embodiment of the device according to the invention, measured quantitative blood supply parameters of body parts and/or their combination are automatically compared with respective statistical average ranges of change of similar parameters for healthy organisms and/or organisms with known pathologies. These operations are performed by the comparator 40 incorporated in the computing unit of the device (FIGS. 3 and 8). The comparator 40 establishes the fact of an agreement or disagreement between each quantitative blood supply parameter and the respective statistical average range of change of that parameter, which is done with the aid of comparison circuits and decoders. The result of the comparison is indicative of the presence or absence of a pathology in the cardiovascular system of the organism being investigated. The boundaries of said ranges are entered in advance into the comparison range memory unit 39 by the comparison range input unit 38. The output signal of the comparator 40 is sent to the recording unit 4 which records the result of the comparison either by displaying the name of a disease or in some other way. One of the preferred embodiments of the comparator 40 is described below.

In invetigating two body parts according to one of the embodiments of the present invention, the comparison range input unit 38 (FIG. 8) enters four numbers into the comparison range memory unit 39. In investigating the symmetrical areas of the brachial arteries of the left and right arms of a patient, i.e., in measuring the quantitative parameters of the blood supply of each arm ($S_3$ and $S_4$), the total blood supply of both arms ($S_{34}$) derived from the expression (4), and the asymmetry of blood supply of the left and right arms ($A_{34}$) derived from the expression (9), the first two numbers, $\overline{S}_{34\ min}$ and $\overline{S}_{34\ max}$, correspond to the lower and upper boundaries, respectively, of the statistical average range of change of the values of the quantitative parameter of the total blood supply of both arms established for healthy subjects of the same sex and age group as the patient. The two other numbers, $\overline{A}_{34\ min}$ and $\overline{A}_{34\ max}$, correspond to the loser and upper boundaries, respectively, of the statistical average range of change of the values of the quantitative parameter of the asymmetry of blood supply of the left and right arms, also established for healthy subjects of the same sex and age group as the patient. The dashes which cap the A and B signify mean values produced by averaging. From the output of the first adder 31 of the addition and division unit 30, a signal is applied to the signal input of the comparison circuit 41 which serves to compare measured values with the first comparison range. The signal corresponds to the quantitative parameter of the total blood supply $S_{34}$ of the left and right ams of the patient. To the first and second threshold inputs of the comparison circuit 41, electric potentials are applied from the comparison range memory unit 39, which are proportional to the lower and upper boundaries, $\overline{S}_{34\ min}$ and $\overline{S}_{34\ max}$, respectively, of the corresponding statistical average range for healthy subjects. If the measured quantitative parameter of the total blood supply value $S_{34}$ is in this range, i.e., if $$\overline{S}_{34\ min} \leq S_{34} \leq \overline{S}_{34\ max}, \tag{16}$$

"1" is produced at the output of the comparison circuit 41. If the above condition is not met, i.e., if $$S_{34} < \overline{S}_{34\ min} \text{ or } S_{34} > \overline{S}_{34\ max}, \tag{17}$$

"0" is produced at the output of the comparison circuit 41.

A signal corresponding to the measured quantitative parameter of the asymmetry $A_{34}$ of the blood supply of the left and right arms of the patient is applied from the output of the first divider 32 of the addition and division unit 30 to the signal input of the comparison circuit 42 which serves to compare blood supply data with the second comparison range. To the first and second threshold inputs of the comparison circuit 42, electric potentials are applied from the respective outputs of the comparison range memory unit 39, which are proportional to the lower and upper boundaries, $\overline{A}_{34\ min}$ and $\overline{A}_{34\ max}$, respectively, of the corresponding statistical average range for healthy subjects.

If the measured quantitative parameter of the asymmetry of blood supply is in this range, i.e., if $$\overline{A}_{34\ min} \leq A_{34} \leq \overline{A}_{34\ max}, \tag{18}$$

"1" is produced at the output of the comparison circuit 42. If the above condition is not satisfied, i.e., if $$A_{34} < \overline{A}_{34\ min} \text{ or } A_{34} > \overline{A}_{34\ max}, \tag{19}$$

"0" is produced at the output of the comparison circuit 42.

The output potentials of the comparison circuits 41 and 42 are applied to the respective inputs of the NAND gate 43. "0" is produced at the output of the NAND gate 43 if the conditions (16) and (18) are satisfied.

If both or either of the conditions (17) and (19) are satisfied, "1" is produced at the output of the NAND gate 43. This output potential is recorded as an alarm signal by the recording unit 4. An alarm signal is produced if the total blood supply of both arms of the patient and the quantitative parameters of the asymmetry of their blood supply are beyond the statistical average ranges of change of these parameters established for healthy subjects.

The determination of the state of the cardiovascular system by investigating both arms of a subject is recommended for preventive examination of certain groups of patients.

In using the method according to the invention for determining the state of the cardiovascular system for a simplified differential diagnosis of atherosclerosis of arteries supplying blood to the lower extremities of man, one can employ the embodiment of the device according to the invention shown in FIGS. 3, 8 and 9. In this device, the comparator 40 differs from the version described above in that the NAND gate 43 is replaced by a two-input AND gate, and in that the signal inputs of the comparison circuits 41 and 42, which serve to compare blood supply data with the first and second comparison ranges, respectively, are connected to the output of the fourth adder 35 of the addition and division unit 30 (FIG. 9) and the output of the third divider 37, respectively. The first input of the divider 37 is connected to the output of the first adder 31 which serves to add quantitative parameters characterizing the supply of blood to both sides of the head. The second input is connected to the output of the first adder 31 which serves to add quantitative parameters characterizing the supply of blood to both legs. Four numbers are entered in the comparison range memory unit 39. Two of these, $S_{\Sigma\ min}$ and $S_{\Sigma\ max}$, correspond to the lower and upper boundaries, respectively, of the statistical average range of the values of the quantitative parameter of the total blood supply of all the six body parts being investigated of patients suffering from atherosclerosis of arteries supplying blood to the quantitative parameters of the lower extremities. The two other numbers, $\overline{B}_{56\ min}$ and $\overline{B}_{56\ max}$, correspond to the lower and upper boundaries, respectively, of the statistical average range for the values of the quantitative parameter of the supply of blood to the left and right legs in relation to the total blood supply of both sides of the head in cases of atherosclerosis of arteries supplying blood to the lower extremities. "1" is produced at the output of the two-input AND gate and recorded by the recording unit 4 as a signal indicative of atherosclerosis if the following conditions are met:

$$\overline{S}_{93\ min} \leq S_{93} \leq \overline{S}_{\Sigma\ max}, \text{ and}$$

$$\overline{B}_{56\ min} \leq B_{56} \leq \overline{B}_{56\ max},$$

where $S_\Sigma$ is a quantitative parameter of the total blood supply of all the six body parts being investigated, and $B_{56}$ is a quantitative parameter of the supply of blood to both legs in relation to the total blood supply of both sides of the head.

All other embodiments of the device in accordance with the invention may incorporate similar computing units 29.

A still another embodiment of the invention is characterized in that apart from other blood supply parameters, one also measures the tachooscillation separation time. All the units of this device are designed and operate as described above with the exception of the tachooscillation separation time measuring unit 44 and the fourth divider 45.

A square pulse shown in FIG. 1h is applied from the third output of the control unit 9 to the input of the tachooscillation separation time measuring unit 44. The duration of thus pulse is equal to the tachooscillation separation time, because its edges coincide with instants $t_1$ and $t_2$ when the separation of tachooscillations begins and ends, respectively. At the output of the tachooscillation separation time measuring unit 44 a signal is produced which is proportional to the above time interval: $T = t_2 - t_1$. This signal is applied to the second input of each divider 45 of a respective blood supply quantitative parameter measuring channel 5. To the first input of each divider 45, a signal is applied from the output of the respective unit 6, which corresponds to a measured blood supply parameter, i.e., the sum total of the absolute areas of all positive and negative half-waves of separated tachooscillations. The fourth divider 45 of each channel 5 divides the quantitative parameter by T. As a result, at the output of the divider 45 there is produced a signal corresponding to the quantitative blood supply parameter divided by T. Such signals are processed, recorded and used as other data which are not related to time.

In the embodiment of FIG. 11, all the operations in connection with the determination of quantitative blood supply parameters of body parts being investigated, the calculation of quantitative blood supply parameters of selected combinations of body parts, and the comparison of blood supply data with statistical average ranges established for healthy subjects and patients with known pathologies are performed by the microprocessor unit 47 which serves to process tachooscillations. In this device, the variable pressure source 1, occlusion cuff 2, and tachooscillation transducer 3, which are incorporated in the tachooscillation separation channel 46, as well as the air distributor 7, pressure transducer 8 and control unit 9 all operate as described above. The output signals of the tachooscillations transducers 3 are output signals of the respective tachooscillation separation channels 46, which are applied to the respective signal inputs of the microprocessor unit 47.

The unit 47 operates in accordance with a program stored by the ROM 51 and selected from a set of programs by pushing a button at the mechanical input 58 of the switch 52 of the ROM 51. The program envisages the use of a certain number of tachooscillation separation channels 46, which corresponds to the number of body parts being investigated.

The microprocessor unit 47 operates as follows. The device according to the invention is actuated by pushing the button 22 of the control unit 9 (FIG. 5), whereupon a short control pulse shown in FIG. 1g is applied from the second output of the control unit 9 to the control input of the microprocessor 48 (FIG. 12). This pulse actuates the microprocessor unit 47 which serves to process tachooscillations. The gating and analog-digital conversion of the input signals applied to the input multiplexer 53 are carried out by said input multiplexer 53 and the analog-digital converter 54, respectively, which are controlled by the microprocessor 48 through the respective interfaces 56 and 55. With the aid of the main memory 50, the microprocessor 48 calculates a value for each tachooscillation separation channel 46, which is proportional to the sum total of the absolute area of all positive and negative half-waves of the separated tachooscillations. In addition, the microprocessor 48 measures the duration of the "1" control potential applied to the input multiplexer 53 from the third output of the control unit 9 and determining the duration of the separation of tachooscillations. As soon as the "1" potential is changed by a "0" potential, the microprocessor 48 switches off the input multiplexer 53 and divides the measured quantitative blood supply parameters by the tachooscillation separation time. The microprocessor 48 further calculates quantitative blood supply parameters according to the expressions (2) . . . (15) and compares them with the respective statistical average ranges of change of these parameters for healthy subjects and patients with known pathologies of the cardiovascular system, which ranges have been entered in advance in the ROM 51. The algorithm of calculating quantitative blood supply parameters and comparing them with respective statistical average ranges is determined by a specific operating program of the microprocessor 48, which is selected with the aid of the switch 52 of the ROM 51 from the set of programs entered in the ROM 51. The selection of a program is done by switching the switch 52 through its input 58. The microprocessor 48 then sends the results of the calculations via the output interface 57 to the recording unit 4.

The operating speed of the existing microprocessors provides for real-time processing of signals arriving from several tachooscillation separation channels 46.

Operation of the occlusion cuff 2 according to the present invention is described above while dealing with the embodiments of the device of this invention intended for investigating at least one and at least two body parts of a patient, respectively.

A better understanding of the invention will be had from a consideration of the following examples.

EXAMPLE 1

Patient P., aged 46 years. Height 172 cm, weight 68 kg, occupation: driver. Case History No 5283/81 at the Vishnevsky Institute of Surgery of the Academy of Medical Sciences of the USSR.

Clinical Diagnosis:

Atherosclerosis of the abdominal aorta, occlusion of the right femoral-popliteal segment. The stage of subcompensation of the arterial blood flow, trophic skin lesions in the ungual phalanx area of the first toe of the right foot.

Case History:

The disease began six months ago with attacks of intermittent claudication on the right side every ten meters and with pain in the right musculus gastrocnemius at rest. The disease rapidly developed, leading to a trophic disorder of the first toe of the right foot. The left foot did not trouble the patient. He underwent a course of conservative therapy at an outpatient clinic with a good result. The pain in the musculus gastrocnemius disappeared, and the attacks of intermittent claudication occurred after covering a distance of one kilometer. The patient was sent to the Vishnevsky Institute of Surgery for examination and treatment.

Translumbar Aortography Data:

S-shaped deformation of the abdominal aorta, occlusion of the right surface femoral and popliteal artery. No changes in the main arteries of the lower left extremity.

Results of Processing Tachooscillations of Three Pair of Symmetrical Body Parts:

The following quantitative blood supply parameters were measured and recorded: left side of the head (the temperal artery area), $S_1 = 100$ arbitrary units; right side of the head, $S_2 = 150$ arbitrary units; left arm (the brachial artery area), $S_3 = 350$ arbitrary units; right arm, $S_4 = 400$ arbitrary units; left shin, $S_5 = 150$ arbitrary units; right shin, $S_6 = 40$ arbitrary units.

The following total blood supply parameters were measured and recorded; the total blood supply of the head, $S_{12} = S_1 + S_2 = 200$ arbitary units; the total blood supply of both shins, $S_{56} = S_5 + S_6 = 190$ arbitrary units; the blood supply of both shins in relation to the total blood supply of the head, $B_{56} = S_{56}/S_{12} = 0.87$; the total blood supply of all the six body parts under investigation, i.e., the head, both arms, and both shins, $S = S_1 + S_2 + S_3 + S_4 + S_5 + S_6 = 1160$ arbitrary units.

The quantitative parameters of the blood supply of the left hip ($S_7$) and that of the right hip ($S_8$) were also measured and recorded. $S_7 = 150$ arbitrary units, $S_8 = 100$ arbitrary units. The asymmetry of the blood supply of both hips was measured: $A_{78} = S_7/S_8 = 1.5$.

It had been earlier established that $\bar{S}_\Sigma$, i.e., the statistical average value of the quantitative parameter of the total supply of blood of the same six symmetrical body parts (the head, arms, and shins) for healthy subjects of the same sex and age group is equal to 2100 arbitrary units.

Conclusions Drawn from the Analysis of the Quantitative Blood Supply Parameters:

1. The quantitative parameters of the total blood supply of all the six investigated symmetrical body parts ($S_\Sigma$) and the ratio between the blood supply of both shins and the total blood supply of the head ($B_{56}$) fall within the statistical average ranges for patients of the same sex and age group suffering from atherosclerosis of the arteries supplying blood to the lower extremities, i.e., the ranges of $(40 \ldots 80)\%$ $\bar{S}_\Sigma = (840 \ldots 1680)$ arbitrary units for $S_\Sigma$ and $0.3 \ldots 2$ for $B_{56}$.

The diagnosis made on the basis of tachooscillation processing points to atherosclerosis of the blood vessels supplying blood to the lower extremities.

The diagnosis was confirmed by translumbar aortography data. It must be noted in this connection that translumbar aortography requires much more time than the diagnostic method according to the invention, not to mention that it calls for sophisticated and expensive equipment and a modern laboratory staffed with qualified personnel. Furthermore, translumbar aortography is an invasive technique, wherefore it is harmful to the patient.

The diagnostic method in accordance with the invention is advantageous over translumbar aortography in that it requires measurements which take a mere 40 to 60 seconds. The device according to the invention takes these measurements automatically without doing any harm to the patient.

2. The quantitative reduction in the blood supply of the right leg as the occluding cuff was moved from the hip to the shin from $S_8 = 100$ arbitrary units to $S_6 = 40$ arbitary units, is a more than two-fold reduction which points to manifest stenosis of the arteries of that leg. This was corroborated by translumbar aortography data, although it must be pointed out that the method according to the invention provides for a quicker and non-invasive diagnosis which is just as accurate.

3. The slight asymmetry of the blood supply of the left and right legs of the patient ($A_{78} = 1.5$) accompanied by manifest stenosis of the arteries of the right leg is indicative of pathology in the blood supply of the left leg as well.

Translumbar aortography did not detect this phenomenon, which points to a lower accuracy of that invasive technique, as compared with the method in accordance with the invention.

EXAMPLE 2

Patient S., aged 43 years. Height 180 cm, weight 62 kg, occupation: construction worker. Case History No 626/82 at the Vishnevsky Institute of Surgery of the Academy of Medical Sciences of the USSR.

Clinical Diagnosis:

Atherosclerosis of the abdominal part of the aorta with a manifest affliction of the iliac segment on both sides (occlusion of the left and stenosis on the right in the area of the bifurcation of the iliac artery).

Case History:

The patient has been afflicted for three years and undergone treatment at an outpatient clinic. Despite the treatment, the disease developed at a fast rate, so the patient was admitted to the Vishnevsky Institute.

Translumbar Aortography Data:

The abdominal aorta has smooth edges, without any change in its bifurcation. The external iliac artery is occluded on the left with constricted sections on the right. The femoral arteries are strongly constricted, but the flow of blood is still possible. The blood flow is maintained through the popliteal arteries and the arteries of the shin.

Results of Processing Three Pair of Symmetrical Body Parts:

The following quantitative blood supply parameters were measured and recorded:

the total blood supply of the head (left and right temperal areas), $S_{12} = 330$ arbitrary units;

the total blood supply of both arms (the areas of the brachial arteries), $S_{34} = 950$ arbitrary units;

the total blood supply of both shins, $S_{56}=125$ arbitrary units.

Also calculated were the quantitative parameters of the total blood supply of six symmetrical body parts ($S_\Sigma=S_{12}+S_{34}+S_{56}=1405$ arbitrary units) and the blood supply of both shins in relation to the total blood supply of the head ($B_{56}=S_{56}/S_{12}=0.38$).

Conclusions:

The processing of tachooscillations confirms the advantages of the present invention which provides for an accurate and non-invasive diagnosis (atherosclerosis of the arteries supplying blood to the lower extremities) through a single measurement cycle taking a mere 40 to 60 seconds.

The quantitative parameters of the total blood supply of all the six investigated body parts ($S_\Sigma$) and the blood supply of both shins in relation to the total blood supply of the head ($B_{56}$) fall within the statistical average range for patients suffering from the above-mentioned disease (see Example 1).

EXAMPLE 3

Patient M., aged 50 years. Height 171 cm, weight 70 kg, occupation: packer. Case History No 551/82 at the Vishnevsky Institute of Surgery of the Academy of Medical Sciences of the USSR Clinical Diagnosis:

Atherosclerosis of the abdominal aorta, stenosis of the iliac and external femoral arteries on both sides, occlusion of the artery of the right shin.

Case History:

The patient has been afflicted for 11 years and undergone treatment at an outpatient clinic, taking vasodilative drugs and receiving physiotherapeutic treatment. The disease developed at a slow rate. The patient was admitted to the Vishevsky Institute for further treatment.

Life History:

The patient was borne into a large family and lived through starvation and other hardships as an evacuee during World War II.

Translumbar Aortography Data:

The edges of the iliac arteries are not smooth. The extreme iliac artery on the right side is stenosed to 40 percent of its diameter over a length of 1 cm. There is also stenosis of both external femoral arteries. The arteries of the left shin are affected. The filling of the arteries of the right shin is retrograde, i.e., these arteries are filled through the collaterals.

Results of Processing Tachooscillations of Three Pair of Symmetrical Body Parts:

The following quantitative blood supply parameters were measured and recorded:

the total blood supply of the head (the left and right temporal areas), $S_{12}=180$ arbitrary units;

the total blood supply of both arms (the areas of the brachial arteries), $S_{34}=700$ arbitrary units;

the total blood supply of both shins, $S_{56}=170$ arbitrary units.

Also calculated were the quantitative parameters of the total blood supply of all the six investigated body parts, $S_{93}=S_{12}+S_{34}+S_{56}=1050$ arbitrary units, and the blood supply of both shins in relation to the total blood supply of the head, $B_{56}=S_{56}/S_{12}=0.94$.

Other quantitative blood supply parameters measured and recorded include the blood supply of the left shin ($S_5=150$ arbitrary units), the blood supply of the right shin ($S_6=20$ arbitrary units), the blood supply of the left hip ($S_7=200$ arbitrary units), and the blood supply of the right hip ($S_8=185$ arbitrary units).

$S_8/S_6=9.25$.

It was pointed out above that a more than 5-fold difference between the quantitative blood supply parameters measured in different areas of an extremity or between a measured blood supply parameter and the norm is indicative of an occlusion of the artery supplying blood to the extremity.

A comparison of the above quantitative blood supply parameters with the corresponding statistical average ranges (see Example 1) shows that the present invention provides for an easy, quick and accurate diagnosis of atherosclerosis of arteries supplying blood to the lower extremities and of an occlusion of the artery of the patient's right extremity.

EXAMPLE 4

Patient G., aged 41 years, a former fitter, Category II of invalidity, Case History No 12,622 at the Fourth Gradskaya Clinic of Moscow.

Clinical Diagnosis:

Leriche's syndrome (thrombotic occlusion of the distal aorta), pulmonary hypertension, insufficient arterial pulse.

Case History:

The patient has been ill since 1973. A sharp deterioration of his state occurred in 1982 (general weakness, pain in the legs and abdomen, the absence of arterial pulse in the shins, partial asphyxiation). Hospitalized on Sept. 4, 1982. The treatment included the administration of cardiac glycosides, vitamins, cerebrolysin, injections of solcoseril, etc.). These measures helped improve the state of the patient. The arterial pulse in the shins was restored and the patient could walk again. He was subsequently treated at an outpatient clinic.

The Dynamics of Quantitative Blood Supply Parameters Following the Processing of Tachooscillations of Three Pair of Symmetrical Body Parts (the head, arms, and shins):

| | Date of Measurement | | |
|---|---|---|---|
| | Sept. 8, 1982 | Oct. 1, 1982 | Nov. 25, 1982 |
| Total Blood Supply of All the Six Body Parts, $S_\Sigma$ (measured in arbitrary units) | 803 | 1090 | 1417 |
| Blood Supply of Both Shins Versus the Total Blood Supply of the Head, $B_{56}$ | 1 | 1 | 3 |

The above examples are a clear indication of important advantages of the method and device in accordance with the invention.

The use of occluding cuffs for picking up physiological signals rules out the necessity of a surgical intervention and the action on the organism of electromagnetic or other fields. As a result, the measurement taking procedure is totally harmless to the organism.

The invention makes it possible to carry out repeated examinations of combinations of body parts, which considerably improves the information content of measurements and enables the physician to follow the dynamics of the state of the cardiovascular system.

The invention makes it possible to calculate new quantities corresponding to the sum total of the absolute values of the areas of positive and negative half-waves of tachooscillations separated during a single cycle of change of pressure applied to the body parts being investigated. Calculating such quantities for each body part being investigated provides highly informative hemodynamic parameters which characterize the current state of the heart, the state of the blood vessels of the body part being investigated, and the degree of nervous regulation of the cardiovascular system. Measurement of blood supply parameters for combinations of pairs of symmetrical body parts makes i it possible to obtain a new set of hemodynamic parameters, such as the total blood supply of all body parts being investigated and of combinations thereof, the asymmetry of blood supply of each pair of symmetrical body parts, and the difference between the blood supply of a body part and certain combinations of body parts.

The possibility of selecting different body parts for investigation and of analyzing a large number of new hemodynamic parameters makes the method and device of this invention highly flexible and provides for a highly accurate diagnosis of the state of the cardiovascular system of a patient. The invention has made it possible to develop new effective criteria for evaluating the state of the cardiovascular system as a whole and the state of blood vessels of individual parts of an organism.

The device according to the invention is easy to operate and provides for full automation with regard to the processing of diagnostic data. Furthermore, it is self-powered and small in size. Such devices can be provided with battery power packs and operated by medical personnel of medium qualification. When used by highly qualified medical personnel, a device of thus type can yield a wealth of new data on the state of the cardiovascular system.

The latest research points to the following applications of the method and device according to the present invention:
- a fast and accurate differential diagnosis of a broad range of cardiovascular diseases, such as cardiac ischemia, arterial hypertension, neurocirculatory asthenia, atherosclerosis of arteries, sexual impotence, etc. The invention cuts down the time required for making a diagnosis and ensures a correct selection of a course of treatment;
- monitoring the effectiveness of treatment, including a selection of an optimum type and dose of drugs for each patient, which makes it possible to save on drugs and speed up the treatment;
- forecasting changes in the state of gravely ill hospitalized patients, which makes it possible to reduce the number of fatal outcomes and grave outcomes, such as amputations of extremities;
- detecting the initial stage of a pathology in the state of the cardiovascular system during a preventive examination in the absence of any complaints on the part of a patient and with normal hemodynamic parameters, such as ECG data, arterial pressure, etc.;
- testing new drugs on experimental animals without killing the latter, which helps bring down the overall costs of testing;
- testing individuals with regard to their fitness for a certain profession or occupation (pilots, drivers, divers, athletes, etc.);
- self-monitoring of the state of the cardiovascular system by patients in their homes;
- determination and distribution of training loads for atheltes;
- research in medicine and veterinary science;
- teaching at higher and secondary schools of medicine.

The above list is far from exhausting all the capabilties and applications of the method and device in accordance with the invention, nor does it fully describe all their advantages and positive effects.

Industrial Applicability

The method and device according to the invention can be used in general and outpatient clinics, by ambulance personnel, at laboratories, research institutes and other medical and veterinary establishments for a rapid and accurate evaluation of the current state of the cardiovascular system of man or a warmblooded animal, for the dynamic monitoring of the state of the cardiovascular system in the course of treatment, for analyzing the reaction of the organism to different types of treatment and various external factors, etc.

The invention is best applicable to differential diagnosis of a wide range of disorders of the cardiovascular system, to the selection of optimum types and doses of drugs and optimum treatment procedures, to the development and testing of new drugs, to preventive examinations, to the monitoring of the state of pilots, drivers and athletes, and to self-monitoring of the state of the cardiovascular system by patients in their homes.

The broad functional capabilities of the device according to the invention and the simplicity of its use guarantee a large market for such devices.

The device according to the invention can be produced on a mass scale, for it incorporates well-known and rather simple electronic and pneumonic elements.

We claim:

1. A method for determining the state of the cardiovascular system of an organism being investigated, comprising the following steps:
   applying variable pressure to at least one body part being investigated in the area of a blood vessel;
   converting, while said applied pressure varies, the pulsed oscillations, caused by pulsation of pressure inside said blood vessel of said body part being investigated, into an electrical signal corresponding to the first time derivative of said pulsed oscillations, said signal being tachooscillations having positive and negative half-waves;
   measuring the absolute value of the area of each said positive and negative half-wave of tachooscillations;
   summing said absolute values of the areas of all said positive and negative half-waves of tachooscillations;
   measuring the quantity corresponding to the sum total of absolute values of the areas, this quantity being the quantitative parameter of the blood supply of said body part being investigated;
   recording said quantitative parameter;
   comparing said quantitative parameter with a plurality of statistical ranges of quantitative parameters of the same body part for healthy organisms and organisms with known pathologies respectively; and
   determining the statistical range of said quantitative parameter of said organism being investigated and classifying said organism being investigated with healthy organisms or with organisms with known pathologies.

2. A device for determining the state of the cardiovascular system of an organism being investigated, comprising:
means for applying a variable pressure to at least one body part of said organism being investigated;
an occlusion cuff as part of said means for applying, said cuff disposed over a blood vessel in said body part such that said cuff provides an output indicative of pulsed oscillations of said blood vessel during the application of said variable pressure;
a tachooscillation transducer means connected to said output of said occlusion cuff for converting the pulsed oscillations therefrom into electrical signals corresponding to the first time derivative of said pulsed oscillations, said electrical signals having positive and negative half-waves;
a blood supply quantitative parameter determination means, receiving said electrical signals from said tachooscillation transducer means, for measuring the absolute value of the area of each of said positive and negative half-wave and for summing said absolute values of the areas of all said positive and negative half-waves as a quantity; and,
recording means for recording said quantity as a blood supply quantitative parameter.

3. A method for determining the state of the cardiovascular system, comprising the following steps:
applying variable pressure to at least one body part being investigated in the area of a blood vessel;
converting, as said applied pressure varies, the pulsed oscillations caused by pulsation of pressure inside said blood vessel of the body part being investigated into electrical signals corresponding to the first time derivative of said pulsed oscillations, said signals being tachooscillations having positive and negative half-waves;
measuring the absolute value of the area of each said positive and negative half-wave of tachooscillations;
summing of absolute values of the areas of all said positive and negative half-waves of tachooscillations;
measuring the quantity corresponding to the sum total of absolute values of the areas of all positive and negative half-waves of tachooscillations, this quantity being the quantitative parameter of the blood supply of said body part being investigated;
recording said quantitative parameter of the blood supply of the body part being investigated;
providing sets of statistical data on the distribution of the values of the quantitative parameter of the blood supply of the body part being investigated for control groups of healthy organisms and organisms with known pathologies respectively;
providing statistical average ranges of distribution of the values of said quantitative parameter of the blood supply of the body part being investigated for said healthy organisms and organisms with known pathologies respectively;
comparing said quantitative parameter of the blood supply of said body part of an organism being investigated with said average statistical ranges of distribution of the values of said quantitative parameter of the blood supply of the same body part for said healthy organisms and organisms with known pathologies respectively;
finding the average statistical range to which belongs said quantitative parameter of the blood supply of said body part of said organism being investigated;
determining on the basis of said average statistical range as to the presence or absence of deviations from the norm of said quantitative parameter of the blood supply of said body part of the organism being investigated, which is indicative of the presence or absence of a specified pathology in the cardiovascular system of the organism being investigated.

4. A method as claimed in claim 3, comprising the following additional steps:
applying said variable pressure simultaneously to at least two body parts being investigated;
summing of said quantitative parameters of the blood supply of all body parts being investigated;
recording the sum of said quantitative parameters of the blood supply of all investigated body parts as a further quantitative parameter of the total blood supply of all body parts being investigated;
providing sets of statistical data on the distribution of the values of said further quantitative parameter of the total blood supply of all investigated body parts for said healthy organisms and organisms with known pathologies respectively;
providing the average statistical ranges of distribution of the values of said further quantitative parameter of the total blood supply of all investigated body parts for said healthy organisms and organisms with known pathologies respectively;
comparing said further quantitative parameter of the total blood supply of all investigated body parts of said investigated organisms with said average statistical ranges of distribution of the values of said further quantitative parameter of the total blood supply of the same investigated body parts for said healthy organisms and organisms with known pathologies respectively;
finding the average statistical range to which belongs said further quantitative parameter of the total blood supply of all investigated body parts of said investigated organism;
determining, on the basis of said respective average statistical range, the presence or absence of deviations from the norm of said further quantitative parameter of the total blood supply of all investigated body parts of said investigated organism, which is indicative of the presence or absence of a specific pathology in the cardiovascular system of said organism being investigated.

5. A method as claimed in claim 4, comprising the following additional steps:
calculating the ratio of said quantitative parameter of the blood supply of each said investigated body part to said further quantitative parameter of the total blood supply of all body parts being investigated;
recording the ratio of said quantitative parameter of the blood supply of each said investigated body part to said further quantitative parameter of the total blood supply of all investigated body parts as an additional quantitative parameter of the relative blood supply of the respective investigated body part;
providing sets of statistical data on the distribution of the values of said additional quantitative parameter of the relative blood supply of each investigated body part for said healthy organisms and organisms with known pathologies respectively;

providing the average statistical ranges of distribution of the values of said additional quantitative parameter of the relative blood supply of each said investigated body part for said healthy organisms and organisms with known pathologies respectively;

comparing said additional quantitative parameter of the relative blood supply of each said investigated body part of said investigated organism to said average statistical ranges of distribution of the values of said additional quantitative parameter of the relative blood supply of the same investigated body part for said healthy organisms and organisms with known pathologies respectively;

finding the average statistical ranges to which belong said additional quantitative parameters of the relative blood supply of the investigated body parts of said investigated organism respectively;

determining on the basis of the totality of said average statistical ranges as to the presence or absence of deviations from the norm in the distribution of the blood supply in the investigated body parts of said investigated organism, the presence or absence of a pathology in the cardiovascular system of said organism.

6. A method as claimed in claim 3, comprising the following additional steps:

measuring the duration of a time interval of summation of said absolute values of the areas of all said positive and negative half-waves of tachooscillations;

calculating the ratio of a first quantity, which corresponds to said sum of the absolute values of the areas of all said positive and negative half-waves of tachooscillations for each said investigated body part, to the measured duration of said time interval;

recording the ratio of said first quantity for each said investigated body part to the measured duration of said time interval as a first quantitative parameter of the blood supply of each body part being investigated.

7. A method for determining the state of the cardiovascular system, comprising the following steps:

applying variable pressure simultaneously to at least two pairs of symmetrical body parts being investigated in the areas of respective blood vessels;

for each said body part being investigated:

converting the pulsed oscillations, caused by pulsations of pressure inside the blood vessel of said body part being investigated, as the applied pressure varies, into electrical signals which correspond to the first time derivative of said pulsed oscillations, said signals being tachooscillations having positive and negative half-waves;

measuring the absolute value of the area of each said positive and negative half-wave of tachooscillations;

summing the absolute values of the areas of all said positive and negative half-waves of tachooscillations;

measuring the quantity which corresponds to the sum of the absolute values of the areas of all said positive and negative half-waves of tachooscillations, said quantity being a quantitative parameter of the blood supply of said body part being investigated;

recording said quantitative parameter of the blood supply of the body part being investigated;

for said pairs of body parts being investigated:

summing of said quantitative parameters of the blood supply of the body parts being investigated individually for each said pair of symmetrical body parts;

recording the sum of said quantitative parameters of the blood supply of the body parts being investigated individually for each said pair of symmetrical body parts as the quantitative parameter of the total blood supply of a respective pair of symmetrical body parts being investigated;

calculating a ratio of said quantitative parameter of the total blood supply of each pair of the symmetrical body parts being investigated to said quantitative parameter of the total blood supply of one pair of the symmetrical body parts being investigated;

recording the ratio of said quantitative parameter of the total blood supply of each pair of the symmetrical body parts being investigated to said quantitative parameter of the total blood supply of one pair of the symmetrical body parts being investigated as a quantitative parameter of the relative blood supply of each pair of the symmetrical body parts in reference to the total blood supply of one pair of the symmetrical body parts being investigated;

providing respective sets of statistical data on the distribution of the values of said quantitative parameters of the relative blood supply of respective investigated pairs of the symmetrical body parts in reference to the total blood supply of one pair of investigated symmetrical body parts of a plurality of control groups of healthy organisms and organisms with known pathologies respectively;

providing the average statistical ranges of distribution of the values of said quantitative parameters of the relative blood supply of respective investigated pairs of symmetrical body parts in reference to the total blood supply of one pair of investigated symmetrical body parts for said healthy organisms and organisms with known pathologies respectively;

comparing said quantitative parameter of the relative blood supply of each investigated pair of the symmetrical body parts in reference to the total blood supply of one pair of the symmetrical body parts of an investigated organism to said average statistical ranges of distribution of the values of the quantitative parameters of the relative blood supply of the same investigated pair of the symmetrical body parts in reference to the total blood supply of one pair of investigated symmetrical body parts for said healthy organisms and organisms with known pathologies respectively;

finding average statistical ranges to which belong said quantitative parameters of the relative blood supply of said pairs of the symmetrical body parts being investigated in reference to the total blood supply of one pair of the symmetrical body parts of said investigated organism;

determining on the basis of the totality of said average statistical ranges as to the presence or absence of deviations from the norm in the distribution of the blood supply to said pairs of investigated symmetrical body parts, pointing to the presence or absence of a pathology in the cardiovasuclar system of said organism being investigated.

8. A method as claimed in claim 7, comprising the following additional steps:

summing said quantitative parameters of the blood supply of all left-side investigated body parts;

recording the sum of said quantitative parameters of the blood supply of all left-side investigated body parts as the quantitative parameter of the total blood supply of all left-side investigated body parts;

summing said quantitative parameters of the blood supply of all right-side investigated body parts;

recording the sum of said quantitative parameters of the blood supply of all right-side investigated body parts as the quantitative parameter of the total blood supply of all right-side investigated body parts;

calculating the ratio of said quantitative parameter of the total blood supply of all left-side investigated body parts to said quantitative parameter of the total blood supply of all right-side investigated body parts;

recording the ratio of said quantitative parameter of the total blood supply of all left-side investigated body parts to said quantitative parameter of the total blood supply of all right-side investigated body parts as the quantitative parameter of the relative blood supply of all left-side investigated body parts in reference to the total blood supply of all right-side investigated body parts;

providing respective sets of statistical data on the distribution of the values of said quantitative parameter of the relative blood supply of all left-side body parts being investigated in reference to the total blood supply of all right-side body parts being investigated for said healthy organisms and said organisms with known pathologies respectively;

providing the average statistical ranges of distribution of the values of said quantitative parameter of the relative blood supply of all left-side investigated body parts in reference to the total blood supply of all right-side investigated body parts for said healthy organisms and organisms with known pathologies respectively;

comparing said quantitative parameter of the relative blood supply of all left-side body parts in reference to the total blood supply of all right-side body parts of the organism being investigated to said average statistical ranges of distribution of the values of said quantitative parameter of the relative blood supply of all left-side investigated body parts in reference to the total blood supply of all right-side investigated body parts for said healthy organisms and organisms with known pathologies respectively;

finding the average statistical range which belongs said quantitative parameter of the relative blood supply of all left-side investigated body parts in reference to the total blood supply of all right-side investigated body parts of said organism being investigated; and, determining based upon said average statistical range as to the presence or absence of deviations from the norm in the relative blood supply of all left-side symmetrical body parts being investigated in reference to the total blood supply of all right-side symmetrical body parts being investigated pointing to the presence or absence of a pathology in the cardiovascular system of said investigated organism.

9. A method as claimed in claim 8, comprising the following additional steps in order to determine the state of the cardiovascular system changing with time: recurrent application of said varying pressure to the same body parts being investigated of said investigated organism, and calculation of said quantitative parameters of the relative blood supply of each investigated pair of the symmetrical body parts with reference to the total blood supply of one pair of the investigated symmetrical body parts, and calculation of said quantitative parameter of the relative blood supply of all left investigated body parts with reference to the total blood supply of all right investigated body parts of said organism being investigated;

comparing said quantitative parameters of the relative blood supply of each investigated pair of the symmetrical body parts with reference to the total blood supply of one pair of the investigated symmetrical body parts, and comparing said quantitative parameters of the relative blood supply of all left investigated body parts with reference to the total blood supply of all right investigated body parts of said investigated organism, which had been recorded in previous and subsequent applications of said varying pressure to said investigated body parts of said investigated organism respectively;

determining the change in the state of the cardiovascular system of said investigated organism on the basis of the nature and rate of change of said correlated quantitative parameters of the relative blood supply with reference to one another and to respective average statistical ranges of distribution of the values of respective quantitative parameters of the relative blood supply for said healthy organisms and organisms with known pathologies respectively.

10. A method as claimed in claim 7, wherein said control group of organisms includes organisms with arteriosclerosis of the arteries supplying blood to the lower extremities, of the same sex and age category, the method comprising the following additional steps:

applying variable pressure to the left and right parts of the head, symmetrically in the areas of temporal arteries, to the left and right hands, symmetrically near shoulders in the areas of brachial arteries, and to the left and right legs, symmetrically in the areas of the shin arteries;

summing the measured quantitative parameters of the blood supply of all said six body parts being investigated;

recording the sum of the quantitative parameters of the blood supply of all said six body parts being investigated as the quantitative parameter of the total blood supply of all investigated body parts;

providing sets of statistical data on the distribution of the values of said quantitative parameter of the total blood supply of all investigated body parts for said healthy organisms and organisms with arteriosclerosis of the arteries supplying blood to the lower extremities respectively;

providing the average statistical value of said quantitative parameter of the total blood supply of all investigated body parts for said control group of healthy organisms;

providing the average statistical range of distribution of the values of said quantitative parameter of the total blood supply of all investigated body parts for said organisms suffering from arteriosclerosis of the arteries supplying blood to the lower extremities, whose lower and upper boundaries are figures amounting to, respectively, 40% and 80% of the average statistical value of said quantitative parameter of the total blood supply of all investigated body parts which had been established for healthy organisms;

providing the average statistical range of distribution of values of said quantitive parameter of the relative blood supply of the left and right legs in reference to the total blood supply of both said parts of the head for said organisms with arteriosclerosis of the arteries supplying blood to the lower extremities, the lower and upper boundaries thereof being figures 0.3 and 2;

comparing said quantitative parameter of the total blood supply of all body parts of said patient being investigated to said average statistical range of distribution of the values of said quantitative parameter of the total blood supply of all investigated body parts, which had been established for said organisms with arteriosclerosis of the arteries supplying blood to the lower extremities;

comparing the quantitative parameter of the relative blood supply of the left and right legs in reference to the total blood supply of both said parts of the head of said patient being investigated to said average statistical range of distribution of the values of said quantitative parameter of the relative blood supply of the left and right legs with reference to the total blood supply of both said parts of the head for said organisms with arteriosclerosis of the arteries supplying blood to the lower extremities;

determining as to the presence of arteriosclerosis of the arteries supplying blood to the lower extremities of said patient being investigated, if said quantitative parameter of the total blood supply of all investigated body parts of said patient being investigated falls within said average statistical range of distribution of the values of said quantitative parameter of the total blood supply of all investigated body parts, which is determined for said organisms with arteriosclerosis of the arteries supplying blood to the lower extremities, and said quantitative parameter of the relative blood supply of the left and right legs with reference to the total blood supply of both said parts of the head of said investigated patient falls within said average statistical range of distribution of the values of said quantitative parameter of the relative blood supply of the left and right legs with reference to the total blood supply of both said parts of the head, which is determined for said organisms with arteriosclerosis of the arteries supplying blood to the lower extremities.

11. A method for determining the state of the cardiovascular system, comprising the following steps:

first applying a variable pressure to an extremity being investigated in the area of an artery;

converting the pulsed oscillations caused by pulsations of the blood pressure inside said artery, as said applied pressure varies, into electrical signals which correspond to the first time derivative of said pulsed oscillations, said electrical signals being tachooscillations having positive and negative half-waves;

measuring the absolute value of the area of each said positive and negative half-wave of tachooscillations;

summing the absolute values of the areas of all said positive and negative half-waves of tachooscillations;

measuring the quantity which corresponds to the sum of the absolute values of the areas of all said positive and negative half-waves of tachooscillations, this quantity being the quantitative parameter of the blood supply of said extremity being investigated;

recording said quantitative parameter of the blood supply of said extremity being investigated;

secondly applying said variable pressure to the same extremity being investigated in another area of the same artery, which is lower downstream the normal blood flow in said artery;

converting the pulsed oscillations caused by pulsations of the blood pressure inside said artery, as said applied pressure varies, into electrical signals which correspond to the first time derivative of said pulsed oscillations, said electrical signals being tachooscillations having positive and negative half-waves;

measuring the absolute value of the area of each said positive and negative half-waves of tachooscillations;

summing the absolute values of the areas of all said positive and negative half-waves of tachooscillations;

measuring the quantity which corresponds to the sum of the absolute values of the areas of all said positive and negative half-waves of tachooscillations, said quantity being the quantitative parameter of the blood supply of said extremity being investigated;

recording said quantitative parameter of the blood supply of said extremity being investigated;

calculating the ratio of said quantitative parameter of the blood supply of said extremity being investigated, which had been recorded during said first application of said varying pressure, to said quantitative parameter of the blood supply of the same investigated extremity, which had been recorded during said second application of said varying pressure; and determining whether said artery is medically sound based upon said ratio.

12. A method as claimed in claim 11 further including the steps of:

determining the presence of distinct stenosis of said artery, if said ratio lies within a range limited by numbers 2 and 5 or the absence thereof if said ratio is less than 2;

determining the presence of an occlusion of said artery, if said ratio exceeds number 5 or the absence thereof if said ratio is less than 5.

13. A method for determining the state of the cardiovascular system, comprising the steps of:

simultaneously applying varying pressure to the left and right arms, symmetrically near the shoulders in the areas of the brachial arteries of each said arm;

converting, for each said arm being investigated, the pulsed oscillations caused by pulsations of the blood pressure inside said artery, as the applied pressure varies, into electrical signals which correspond to the first time derivative of said pulsed oscillations, said electrical signals being tachooscillations having positive and negative half-waves.

measuring, for each said arm being investigated, the absolute value of the area of each said positive and negative half-wave of tachooscillations;

summing, for each said investigated arm, the absolute values of the areas of all said positive and negative half-waves of tachooscillations;

measuring, for each said investigated arm, the quantity which corresponds to the sum of the absolute values of the areas of all said positive and negative half-waves of tachooscillations, said quantity being the quantitative parameter of the blood supply of the arm being investigated;

recording said measured quantitative parameter of the blood supply of the left arm and said quantitative parameter of the blood supply of the right arm, respectively;

summing said quantitative parameter of the blood supply of the left arm being investigated with said quantitative parameter of the blood supply of the right arm being investigated;

recording said sum of said quantitative parameter of the blood supply of the left investigated arm and said quantitative parameter of the blood supply of the right investigated arm as a quantitative parameter of the total blood supply of the left and right arms;

providing a set of statistical data on the distribution of the values of said quantitative parameter of the total blood supply of the left and right arms for a control group of healthy organisms of one sex and one age group;

calculating the ratio of said quantitative parameter of the blood supply of said left arm being investigated to said quantitative parameter of the blood supply of the right arm being investigated;

recording of said ratio of said quantitative parameter of the blood supply of the left arm being investigated to said quantitative parameter of the blood supply of the right arm being investigated as the quantitative parameter of asymmetry of the blood supply of the left and right arms;

providing a set of statistical data on the distribution of the values of said quantitative parameter of asymmetry of the blood supply of the left and right arms for said healthy organisms;

providing an average statistical range of distribution of the values of said quantitative parameter of the total blood supply of the left and right arms for said healthy organisms;

providing an average statistical range of distribution of the values of said quantitative parameter of the asymmetry of the blood supply of the left and right arms of said healthy organisms;

comparing said quantitative parameter of the total blood supply of the left and right arms and said quantitative parameter of the asymmetry of the blood supply of the left and right arms of said patient being investigated to respective average statistical ranges of distribution of the values of the quantitative parameter of the total blood supply of the left and right arms and quantitative parameter of the asymmetry of the blood supply of the left and right arms of said healthy organisms;

determining the presence of deviations from the norm in the state of the cardiovascular system of said patient being investigated, if at least one said quantitative parameter of the blood supply of said patient goes beyond the boundaries of the respective average statistical range determined for said healthy organisms, or the absence of deviations from the norm in the state of the cardiovascular system of said patient, if both said quantitative parameters of the blood supply of said patient fall within respective average statistical ranges determined for said healthy organisms.

14. A device for determining the state of the cardiovascular system, comprising:

at least one variable pressure source intended to produce variable pressure applied to at least one body part of a living organism, which being investigated;

at least one channel for measuring a blood supply quantitative parameter of said investigated body part of said living organism, said channel having an air inlet and an output, said air inlet is connected to an outlet of said variable pressure source, said one channel for measuring a blood supply quantitative parameter comprising:

an occlusion cuff whose inlet is said air inlet of said channel, said occlusion cuff adapted to apply said variable pressure to said investigated body part in the area of a blood vessel and to provide an output indicative of pulsed oscillations of said blood vessel during application of said variable pressure;

a tachooscillation transducer whose input is connected to said output of said occlusion cuff, said transducer adapted to convert pulsed oscillations of said blood vessel into electrical signals representing tachooscillations having positive and negative half-waves;

a blood supply quantitative parameter determination unit connected to the output of said tachooscillation transducer, said blood supply quantitative parameter determination unit including means for measuring the absolute value of the area of each said positive and negative half-wave of tachooscillations, means for summing up the absolute values of the areas of said positive and negative half-waves of tachooscillations, and means for measuring a quantity which corresponds to the sum of the absolute values of the areas of all said positive and negative half-waves of tachooscillations and having an output that is the output of said channel; and means for recording said quantity as a blood supply quantitative parameter, said means for recording having at least one input connected to said output of said blood supply quantitative parameter measuring channel.

15. A device for determining the state of the cardiovascular system, comprising:

a variable pressure source adapted to produce variable pressure simultaneously applied to at least two body parts of a living organism, which are being investigated;

an air distributor having an air inlet, a control input, and several outlets whose number corresponds to the number of said body parts being investigated, said air inlet being connected to an outlet of said variable pressure source, said air distributor adapted to supply said variable pressure simultaneously to said body parts being investigated;

a plurality of channels for measuring the blood supply quantitative parameters corresponding to the number of said body parts being investigated, each said blood supply quantitative parameter measuring channel having one channel air inlet, two channel control inputs and one channel output, said channel air inlet is connected to a respective outlet of said air distributor, each said channel is adapted to measure the blood supply quantitative parameter of a respective body part being investigated and comprises:

an occlusion cuff whose inlet is said channel air inlet of the blood supply quantitative parameter measuring channel, said occlusion cuff adapted to apply said variable pressure to said body part being investigated in the area of a blood vessel and to provide an output indicative of pulsed oscillations of said blood vessel during application of said variable pressure;

a tachooscillation transducer whose input is connected to said output of said occlusion cuff, said transducer adapted to convert pulsed oscillations of said blood vessel into electrical signals representing tachooscillations having positive and negative half-waves;

means for determining a blood supply quantitative parameter having one signal input, two control inputs and one output which is said channel output of the blood supply quantitative parameter measuring channel, said signal input is connected to an output of said tachooscillation transducer, said control inputs are respective channel control inputs of said blood supply quantitative parameter measuring channel, said blood supply quantitative parameter determination means adapted to measure the absolute value of the area of each said positive and negative half-wave of tachooscillation from said transducer, to sum the absolute values of the areas of all said positive and negative half-waves of said tachooscillations, and to measure the quantity which corresponds to the sum of the absolute values of the areas of all said positive and negative half-waves of said tachooscillations;

a pressure transducer whose input is connected to the outlet of said variable pressure source, said pressure transducer adapted to convert said variable pressure of said variable source into an electrical signal proportional to said variable pressure;

a control unit whose input is connected to an output of said pressure transducer and having three outputs, the first output is connected to the input of said variable pressure source and said control input of said air distributor; the second and third outputs of said control unit are connected respectively to said channel control inputs of each said blood supply quantitative parameter measuring channel;

a recording unit having several signal inputs and one control input; said control input is connected to said first output of said control unit, respective signal inputs of said recording unit are connected to respective outputs of said blood supply quantitative parameter measuring channels.

16. A device as claimed in claim 15, additionally comprising a computing unit having two groups of inputs and two groups of outputs, inputs of said first group are connected respectively to outputs of said blood supply quantitative parameter measuring channels, while all said outputs of said first and second groups are connected to respective inputs of said recording unit; said computing unit comprises:

an addition and division unit having several inputs and two groups of outputs, said inputs are respective inputs of the first group of said computing unit, while outputs of said first group are respective outputs of said first group of said computing unit;

a comparison range input unit having several inputs which are respective inputs of said second group of inputs of said computing unit, and several outputs; said comparison range input unit adapted to set the boundaries of respective average statistical ranges of distribution of the values of respective quantitative parameters of the blood supply of healthy organisms and organisms with known pathologies;

a comparison range memory unit having several inputs connected respectively to said outputs of said comparison range input unit, and several outputs;

a comparator having two groups of inputs and several outputs, inputs of the first group being connected respectively to said second group of outputs of said addition and division unit, the second group of inputs of the comparator are connected respectively to the outputs of said comparison range memory unit, the outputs of the comparator are respective outputs of said second group of the computing unit, said comparator adapted to compare the quantitative parameters of the blood supply of the organism being investigated to said average statistical ranges of distribution of the values of respective quantitative parameters of the blood supply for healthy organisms and for organisms with known pathologies, and to produce a signal corresponding to the comparison results.

17. A device as claimed in claim 16, wherein said addition and division unit comprises:

a first adder having two inputs which are the inputs of the addition and division unit, and an output which is at the same time one of the outputs of each of said first and second groups of outputs of said addition and division unit, said first adder adapted to calculate the quantitative parameter of the total blood supply of the left and right arms of said patient being investigated;

a first divider having two inputs connected respectively to the like inputs of said first adder, and one output which is another output of each said first and second groups of outputs of said addition and division unit; and wherein said comparator comprises:

a first comparison circuit having three inputs, one input being one of said first group of inputs, while two other inputs are respective inputs of said second group of inputs of said comparator;

a second comparison circuit having three inputs, one input being the other input of said first group of inputs, while two other inputs are respective inputs of said second group of inputs of said comparator;

a NAND gate having two inputs which are connected to said outputs of said first and second comparison circuits, said NAND gate having an output which is said output of said comparator.

18. A device as claimed in claim 16, wherein said addition and division unit comprises:

three first adders having each two inputs, which are respective inputs of said addition and division unit, while outputs of said first adders are simultaneously respective outputs of each of said first and second groups of outputs of said addition and division unit;

three first dividers, each having two inputs, the like inputs of each said first divider are connected respectively to the like said inputs of each respective first adder, while the outputs of said first dividers are simultaneously said respective outputs of each said first and second groups of outputs of said addition and division unit;

a second adder having three inputs which are connected respectively to the first inputs of said first dividers, and an output which is simultaneously the respective output of each said first and second group of outputs of said addition and division unit;

a third adder having three inputs which are connected respectively to the second inputs of said first dividers, and an output which is simultaneously the respective output of each of said first and second groups of outputs of said addition and division unit;

a fourth adder having two inputs connected respectively to said outputs of said second and third adders, and an output which is simultaneously the respective output of each said first and second groups of outputs of said addition and division unit;

a second divider having two inputs connected respectively to the first and second inputs of said fourth adder, and an output which is simultaneously the respective output of each said first and second groups of outputs of said addition and division unit;

two third dividers having each two inputs; the first inputs thereof are connected to said output of the first of said first adders, the second inputs are connected respectively to said outputs of two other said first adders, while the outputs of said third dividers are respective outputs of each of said first and second groups of outputs of said addition and division unit.

* * * * *